US008003124B2

(12) United States Patent
Varner et al.

(10) Patent No.: US 8,003,124 B2
(45) Date of Patent: *Aug. 23, 2011

(54) SUSTAINED RELEASE IMPLANTS AND METHODS FOR SUBRETINAL DELIVERY OF BIOACTIVE AGENTS TO TREAT OR PREVENT RETINAL DISEASE

(75) Inventors: Signe E. Varner, Long Beach, CA (US); Nathan Robert Fox Beeley, Irvine, CA (US); Eugene de Juan, San Franciso, CA (US)

(73) Assignee: Surmodics, Inc., Eden Prairie, MN (US)

( * ) Notice: Subject to any disclaimer, the term of this patent is extended or adjusted under 35 U.S.C. 154(b) by 580 days.

This patent is subject to a terminal disclaimer.

(21) Appl. No.: 11/399,945

(22) Filed: Apr. 7, 2006

(65) Prior Publication Data

US 2006/0257451 A1    Nov. 16, 2006

Related U.S. Application Data

(60) Provisional application No. 60/669,701, filed on Apr. 8, 2005.

(51) Int. Cl.
*A61F 2/00* (2006.01)
(52) U.S. Cl. ...................... 424/427; 604/521; 604/891.1
(58) Field of Classification Search .................. 424/422, 424/468, 426–428; 525/432–434, 354, 176, 525/454, 467; 528/176, 196, 332; 623/6, 623/1.42, 1.46
See application file for complete search history.

(56) References Cited

U.S. PATENT DOCUMENTS

| | | | |
|---|---|---|---|
| 3,598,119 A | 8/1971 | White | |
| 3,659,610 A | 5/1972 | Cimber | |
| 4,300,557 A | 11/1981 | Refojo et al. | |
| 4,645,491 A | 2/1987 | Evans | |
| 4,710,171 A | 12/1987 | Rosenberg | |
| 4,718,905 A * | 1/1988 | Freeman | 623/6.5 |
| 4,781,691 A | 11/1988 | Gross | |
| 4,869,717 A | 9/1989 | Adair | |
| 4,909,784 A | 3/1990 | Dubroff | |
| 4,978,334 A | 12/1990 | Toye et al. | |
| 5,098,443 A | 3/1992 | Parel et al. | |
| 5,207,660 A | 5/1993 | Lincoff | |
| 5,238,481 A | 8/1993 | Takagi et al. | |
| 5,266,562 A | 11/1993 | Mukherjee et al. | |
| 5,273,530 A | 12/1993 | del Cerro et al. | |
| 5,324,519 A | 6/1994 | Dunn et al. | |
| 5,326,345 A | 7/1994 | Price, Jr. | |
| 5,328,481 A | 7/1994 | Wang | |
| 5,378,475 A | 1/1995 | Smith et al. | |
| 5,395,618 A | 3/1995 | Darougar et al. | |
| 5,409,457 A | 4/1995 | del Cerro et al. | |
| 5,466,233 A | 11/1995 | Weiner et al. | |
| 5,487,725 A | 1/1996 | Peyman | |
| 5,516,522 A | 5/1996 | Peyman et al. | |
| 5,599,552 A | 2/1997 | Dunn et al. | |
| 5,658,995 A * | 8/1997 | Kohn et al. | 525/432 |
| 5,665,769 A | 9/1997 | Kato et al. | |
| 5,723,530 A | 3/1998 | Zanzig et al. | |
| 5,725,514 A | 3/1998 | Grinblat et al. | |
| 5,770,589 A | 6/1998 | Billson et al. | |
| 5,773,019 A | 6/1998 | Ashton et al. | |
| 5,792,099 A | 8/1998 | DeCamp et al. | |
| 5,824,685 A | 10/1998 | Campochiaro et al. | |
| 5,827,236 A | 10/1998 | Takahashi | |
| 5,869,079 A | 2/1999 | Wong et al. | |
| 5,871,470 A | 2/1999 | McWha | |
| 5,902,598 A | 5/1999 | Chen et al. | |
| 5,904,144 A | 5/1999 | Hammang et al. | |
| 5,941,250 A | 8/1999 | Aramant et al. | |
| 6,001,386 A | 12/1999 | Ashton et al. | |
| 6,025,329 A | 2/2000 | Utsumi et al. | |
| 6,036,678 A | 3/2000 | Giungo | |
| 6,074,661 A * | 6/2000 | Olejnik et al. | 424/427 |
| 6,075,032 A | 6/2000 | Campochiaro et al. | |
| 6,159,218 A | 12/2000 | Aramant et al. | |
| 6,214,901 B1 | 4/2001 | Chudzik et al. | |
| 6,217,895 B1 | 4/2001 | Guo et al. | |
| 6,254,587 B1 | 7/2001 | Christ et al. | |
| 6,299,603 B1 | 10/2001 | Hecker et al. | |
| 6,309,374 B1 | 10/2001 | Hecker et al. | |
| 6,358,935 B1 | 3/2002 | Beck et al. | |
| 6,375,972 B1 | 4/2002 | Guo et al. | |
| 6,378,526 B1 | 4/2002 | Bowman et al. | |
| 6,397,849 B1 | 6/2002 | Bowman et al. | |
| 6,402,734 B1 | 6/2002 | Weiss | |
| 6,413,245 B1 | 7/2002 | Yaacobi et al. | |
| 6,413,540 B1 | 7/2002 | Yaacobi | |
| 6,436,427 B1 | 8/2002 | Hammang et al. | |
| 6,462,071 B1 | 10/2002 | Castillejos | |
| 6,537,253 B1 | 3/2003 | Haindl | |
| 6,544,249 B1 | 4/2003 | Yu et al. | |
| 6,548,078 B2 | 4/2003 | Guo et al. | |
| 6,579,256 B2 | 6/2003 | Hughes | |
| 6,669,950 B2 | 12/2003 | Yaacobi | |
| 6,669,980 B2 | 12/2003 | Hansen | |
| 6,699,493 B2 | 3/2004 | Wong | |
| 6,713,081 B2 | 3/2004 | Robinson et al. | |

(Continued)

FOREIGN PATENT DOCUMENTS

EP          0417764           3/1991

(Continued)

OTHER PUBLICATIONS

"Biodegradable Polymers as Drug Delivery Systems," Chassin M, Langer R, New York: Dekker; 1990 . 71-119.

(Continued)

*Primary Examiner* — Michael G Hartley
*Assistant Examiner* — Jagadishwas Samala
(74) *Attorney, Agent, or Firm* — Kagan Binder, PLLC

(57) ABSTRACT

The invention relates to sustained release implants and to methods for treating eyes, particularly the eyes of mammals having eye disorders or diseases. By using the implants and methods described herein, the delivery of the one or more bioactive agents can be localized at a desired treatment site, particularly the choroid and the retina.

28 Claims, 14 Drawing Sheets

U.S. PATENT DOCUMENTS

| | | |
|---|---|---|
| 6,719,750 B2 | 4/2004 | Varner et al. |
| 6,750,196 B1 | 6/2004 | Reh et al. |
| 7,226,612 B2 * | 6/2007 | Sohier et al. .................. 424/426 |
| 2001/0008961 A1 | 7/2001 | Hecker et al. |
| 2002/0042652 A1 | 4/2002 | Peyman |
| 2002/0055724 A1 | 5/2002 | Hughes |
| 2002/0061327 A1 | 5/2002 | Hammang et al. |
| 2002/0127250 A1 | 9/2002 | Guo et al. |
| 2002/0139378 A1 | 10/2002 | Trese et al. |
| 2002/0188037 A1 | 12/2002 | Chudzik et al. |
| 2002/0198511 A1 | 12/2002 | Varner et al. |
| 2003/0014036 A1* | 1/2003 | Varner et al. .................. 604/521 |
| 2003/0021828 A1 | 1/2003 | Guo et al. |
| 2003/0064088 A1 | 4/2003 | Carvalho et al. |
| 2003/0069560 A1 | 4/2003 | Adamis et al. |
| 2003/0073597 A1 | 4/2003 | Gallotti et al. |
| 2003/0129215 A1* | 7/2003 | Mollison et al. ............. 424/426 |
| 2003/0158521 A1 | 8/2003 | Ameri |
| 2004/0009222 A1 | 1/2004 | Chou et al. |
| 2004/0022853 A1* | 2/2004 | Ashton et al. .................. 424/468 |
| 2004/0024448 A1* | 2/2004 | Chang et al. .................. 623/1.42 |
| 2004/0047911 A1 | 3/2004 | Lyu et al. |
| 2004/0062875 A1 | 4/2004 | Chappa et al. |
| 2004/0121014 A1 | 6/2004 | Guo et al. |
| 2004/0133155 A1 | 7/2004 | Varner et al. |
| 2004/0175410 A1 | 9/2004 | Ashton et al. |
| 2004/0208910 A1 | 10/2004 | Ashton et al. |
| 2004/0215133 A1 | 10/2004 | Weber et al. |
| 2005/0008695 A1 | 1/2005 | Ashton et al. |
| 2005/0019371 A1 | 1/2005 | Anderson et al. |
| 2005/0025834 A1 | 2/2005 | Guo et al. |
| 2005/0059956 A1 | 3/2005 | Varner et al. |
| 2005/0186279 A1 | 8/2005 | Guo et al. |
| 2005/0196424 A1 | 9/2005 | Chappa et al. |
| 2005/0220839 A1 | 10/2005 | DeWitt et al. |
| 2005/0220840 A1 | 10/2005 | DeWitt et al. |
| 2005/0220841 A1 | 10/2005 | DeWitt et al. |
| 2005/0220842 A1 | 10/2005 | DeWitt et al. |
| 2005/0220843 A1 | 10/2005 | DeWitt et al. |
| 2005/0244459 A1 | 11/2005 | DeWitt et al. |
| 2006/0198868 A1 | 9/2006 | DeWitt et al. |
| 2008/0260803 A1* | 10/2008 | Hughes et al. ................ 424/428 |

FOREIGN PATENT DOCUMENTS

| | | |
|---|---|---|
| EP | 1247537 A1 * | 4/2001 |
| EP | 1484054 | 12/2004 |
| JP | 9136830 | 5/1997 |
| JP | 2003-171315 | 6/2003 |
| JP | 2003-313119 | 6/2003 |
| WO | WO 95/28984 | 11/1995 |
| WO | WO 00/40089 | 7/2000 |
| WO | WO 02/17884 | 3/2002 |
| WO | WO 02/74196 | 9/2002 |
| WO | WO2004/28477 | 4/2004 |
| WO | WO 2004/98565 | 11/2004 |
| WO | WO2005/97228 | 4/2005 |
| WO | WO 2005/99786 | 4/2005 |
| WO | WO 2005/99787 | 4/2005 |
| WO | WO 2006/23130 | 3/2006 |

OTHER PUBLICATIONS

"Hydrogels for the Controlled Release of Pharmaceutical Proteins," Bos, et al., Pharmaceutical Technology, Oct. 2001 p. 110-120, XP002362432.

"Reversible Aggregation of Lysozyme in a Biodegradable Amphiphilic Multiblock Copolymer," European Journal of Pharmaceutics and Biopharmaceutics, Elsevier Science Publishers B.V., vol. 54, No. 1, Jul. 2007 p. 89-93, XP004367696.

"The Effect of Polymer Structure and Formulation Techniques on the Release of Model Peptide," Proceedings of the International Symposium on Controlled Release Bioactive Materials, vol. 22, 1995 p. 522-523, XP009065791.

* cited by examiner

_US 8,003,124 B2_

SUSTAINED RELEASE IMPLANTS AND METHODS FOR SUBRETINAL DELIVERY OF BIOACTIVE AGENTS TO TREAT OR PREVENT RETINAL DISEASE

This application claims the benefit of U.S. Provisional Application Ser. No. 60/669,701, filed Apr. 8, 2005, entitled "SUSTAINED DELIVERY DEVICES FOR THE CHOROID AND RETINA AND METHODS FOR SUBRETINAL ADMINISTRATION OF BIOACTIVE AGENTS TO TREAT AND/OR PREVENT RETINAL DISEASES," which is incorporated herein by reference in its entirety.

FIELD OF THE INVENTION

The present invention relates to sustained release implants and to methods for treating eyes, particularly the eyes of mammals having eye disorders or diseases. More particularly the present invention relates to implants and methods for administering one or more bioactive agents subretinally by the use of one or more implants. By using the implants and methods described herein, the delivery of the one or more bioactive agents can be localized at a desired treatment site, particularly the choroid and the retina.

BACKGROUND OF THE INVENTION

There are a number of vision-threatening disorders or diseases of the eye of a mammal including, but not limited to diseases of the retina, retinal pigment epithelium (RPE) and choroid. Such vision threatening diseases include, for example, ocular neovascularization, ocular inflammation and retinal degenerations. Specific examples of these disease states include diabetic retinopathy, chronic glaucoma, retinal detachment, sickle cell retinopathy, age-related macular degeneration, retinal neovascularization, subretinal neovascularization; rubeosis iritis inflammatory diseases, chronic posterior and pan uveitis, neoplasms, retinoblastoma, pseudoglioma, neovascular glaucoma; neovascularization resulting following a combined vitrectomy and lensectomy, vascular diseases, retinal ischemia, choroidal vascular insufficiency, choroidal thrombosis, neovascularization of the optic nerve, diabetic macular edema, cystoid macular edema, macular edema, retinitis pigmentosa, retinal vein occlusion, proliferative vitreoretinopathy, angioid streak, and retinal artery occlusion, and, neovascularization due to penetration of the eye or ocular injury.

For example, age-related macular degeneration (AMD) is the leading cause of irreversible severe central vision loss in Caucasians fifty years old and older in the United States. According to the 1990 U.S. census, approximately 750,000 people over 65 years of age were estimated as severe visual impairment in one or both eyes from AMD. Also, the number of cases of AMD has been predicted to increase from 2.7 million in 1970 to 7.5 million by the year 2030.

Roughly 80 percent of the AMD cases involve non-neovascular conditions, for which there are no effective treatments. For the remaining cases involving neovascularization, currently available treatments are sub-optimal. Perhaps the best-known therapy is photodynamic therapy (PDT), however, while this therapy has received significant intention in both the ophthalmic and financial investment communities, it is useful in only about 20 percent of neovascular AMD cases. In addition, this particular therapy is not a simple or inexpensive treatment. The procedure generally needs to be repeated every three months for at least two years, with approximate total cost of $12,250.

A number of angiostatic agents are currently under investigation for the treatment of AMD. Thalidomide, for example, is known to be a powerful angiostatic agent. Its systemic side effects, however, include peripheral neuropathy, central nervous system depression, and embryotoxicity. In addition, these systemic side effects have limited the dosage administered to patients for the treatment of subretinal neovascularization. Systemic inhibition of angiogenesis in older patients can also interfere with the development of collateral circulation, which has a role in the prevention of central nervous system as well as cardiac ischemic events.

A number of techniques or methodologies have been developed to deliver drugs to the various tissues or structures that make up the mammalian eye as described hereinafter to treat a wide range of disorders or diseases of the eye. However, delivery of drugs, proteins and the like to the eye(s) of mammals so as to achieve the desired therapeutic or medical effect, especially to the retina and/or the choroid, has proven to be challenging, most of which is owed to the geometry, delicacy and/or behavior of the eye and its components. A brief description of various conventional methods or techniques for delivering drugs to the tissues of the eye and the shortcomings thereof are hereinafter described.

Oral ingestion of a drug or injection of a drug at a site other than the eye can provide a drug systemically; however, such a systemic administration does not provide effective levels of the drug specifically to the eye. In many ophthalmic disorders involving the retina, posterior tract, and optic nerve, adequate levels of the drug cannot be achieved or maintained by oral or parenteral routes of administration. Thus, further and repeated administration of the drug would be necessary to achieve the desired or adequate levels of concentration of the drug. Such further and repeated administrations of such drugs, however, may produce undesired systemic toxicity.

Ophthalmic conditions have also been treated using drugs applied directly to the eye in either liquid or ointment form. This route of administration (i.e., topical administration), however, is most effective in treating problems involving the superficial surface of the eye and diseases that involve the cornea and anterior segment of the eye, such as for example, conjunctivitis. In addition, topical eye drops may drain from the eye through the nasolacrimal duct and into the systemic circulation, further diluting the medication and risking unwanted systemic side effects. Furthermore, delivery of drugs in the form of topical eye drops is also of limited utility because the drug cannot easily cross the cornea or sclera and be made available to the vitreous, retina, or other subretinal structures such as the retinal pigment epithelium ("RPE") or choroidal vasculature and/or is highly unstable and therefore not easily formulated for topical delivery. Moreover, data also indicates that it is not unusual for up to 85% of topically applied agents to be removed by the eye's blink mechanism/reflex.

Direct delivery of drugs to the eye by a topical insert has also been attempted; however, this method is not desirable. Such topical inserts require patient self-administration and thus education on their insertion into and removal from the eye. Consequently, this technique demands a certain degree of manual dexterity that can be problematic for geriatric patients who are particularly susceptible to certain eye disorders that appear age related (e.g., age related macular degeneration). Also, in many instances such topical inserts may cause eye irritation and such inserts are prone to inadvertent loss due to eyelid laxity. In addition, these devices provide a source of drug only to the cornea and anterior chamber, and thus do not provide any significant pharmacologic advantage over topical eye drops or ointments. Thus, such devices have limited utility for providing an effective source of drugs to the vitreous or tissues located in the posterior segment of the eye.

As a consequence most methods for treating eye disorders or diseases in the posterior segment, or the back-of-the-eye, involve intravitreal delivery of the drug. One such technique for intravitreal delivery is accomplished by intraocular injection of the drug or microspheres containing the drug directly into the vitreous or by locating a device or capsule containing the drug in the vitreous, such as that described in U.S. Pat. No. 5,770,589. Intravitreal injection of a drug is an effective means of delivering the drug to the posterior segment of the eye in high concentrations, but it is not without its shortcomings such as fast clearance rate and tissue toxicity.

In addition, it also is well known that many therapeutic drugs cannot easily diffuse across the retina. Thus, the dose being administered and maintained in the vitreous has to take into account the amount that can diffuse across the retinal boundary as well as how long the drug is retained in effective amounts within the vitreous. For example, it has been observed from animal studies that three days following an injection of triamcinolone, less than 1% of the triamcinolone present in the vitreous was associated with other tissues including the retina, pigment epithelium, and sclera. In addition to the relative effectiveness of drug delivery across the barrier, complications or side effects have been observed when using the direct injection into vitreous technique with some therapeutics.

For example, compounds classified as corticosteroids, such as triamcinolone, can effectively treat some forms of neovascularization such as corneal neovascularization. When these compounds were used to treat neovascularization of the posterior segment by direct injection, these compounds were observed to cause undesirable side effects in many patients. The adverse affects or undesirable side effects being observed included elevations in intraocular pressure and the formation of, or acceleration of the development of cataracts. Elevations in intraocular pressure are of particular concern in patients. Moreover, a risk exists that the use of corticosteroids in patients with normal intraocular pressure will cause elevations in pressure that result in damage to ocular tissue. Since therapy with corticosteroids is frequently long term, a potential exists for significant damage to ocular tissue as a result of prolonged elevations in intraocular pressure attributable to that therapy.

Consequently, efforts in the area of intravitreal delivery also have included delivery by locating a sustained release implant, capsule or other such device or mechanism that is in communication with the vitreous and which is configured so as to provide a release over time into the vitreous of the contained drug. Examples of such controlled release devices are described in U.S. Pat. Nos. 6,217,895; 5,773,019; 5,378,475; and in U.S. Patent Application Publication No. 2002/0061327.

A common feature of the techniques/instruments described therein, is that a surgical incision is required to be made at the outset of a procedure so that the implant, capsule or other such device can be inserted through the eye and located in the vitreous. These methods and techniques may also involve the use of sutures following completion of the procedure to seal or close the incision so as to prevent loss of vitreous material and promote wound closure healing. As is known to those skilled in the art, maintaining the volume and pressure of the posterior segment or vitreous is necessary to maintaining the shape and optical arrangement of the eye. Such a course of treatment also increases the duration and cost as well as the realistic risks of corneal ulceration, cataract formation, intraocular infection, and/or vitreous loss that accompany these procedures.

There is described in U.S. Pat. Nos. 5,273,530 and 5,409,457 an instrument and methodology to transplant donor cells, more specifically donor retina cells, in the subretinal space. It also is described therein that the instrument also can be used to inject or remove material from the vitreous. According to the described methodology, the instrument is shaped and dimensioned so it can be inserted into an eye orbit along an insertion path that extends along the periphery of the eye and so as to place the tip adjacent to the retina or subretinal region. The tip is then moved generally in the medial direction so the tip resides in the subretinal region or in the vitreous depending upon how much the tip is moved. In order to prevent over-insertion of the tip, a collar is provided about the tip so as to limit the distance the tip can be inserted into the eye.

There also is described in US Patent Application Publication 2002/0055724, an instrument for subretinal transplantation of retinal cells, epithelium and choroid within their normal planar configuration as a graft into the subretinal region of an eye. The described instrument is inserted into an opening in the eye using either a trans-corneal surgical approach or a trans-choroidal and scleral surgical approach. According to this technique the instrument is advanced under the retina to detach the retina so that the graft can be inserted. As noted in U.S. Pat. No. 5,273,530, the penetration of the anterior part or segment of the eye, using the transcorneal or the transscleral route creates the risks of corneal ulceration, cataract formation and other anterior penetration problems. Also using either approach, a surgical incision is created at the outset of a procedure so that the instrument can be inserted and sutures are used following completion of the procedure to seal or close the incision so as to prevent loss of vitreous material (i.e., aqueous humor).

There is described in U.S. Pat. No. 5,516,522 a biodegradable porous drug delivery device for controllably releasing a pharmacological agent. The device comprises a hollow tube having an interior surface and an exterior surface and a first end and a second end. A pharmacological agent is filled into the hollow tube for controllable release through the channels of the tube. Prior to the pharmacological agent being filled into the hollow tube, the first end is heat sealed, and after the pharmacological agent is filled into the hollow tube, the second end is heat-sealed. There are described in U.S. Pat. Nos. 5,324,519 and 5,599,552 biodegradable polymer compositions composed of a thermoplastic or thermosetting polymer that is injected into the body in a liquid injectable state. These compositions are used to prevent and treat disorders and diseases, such as bone or nerve growth disorders, and to alter body functions (e.g. as birth control). U.S. Pat. No. 5,599,552 further describes using the compositions to enhance regeneration of cells and tissue, such as bone and nerve cells, or for delivery of biologically-active substances to tissue or organs.

Thus, there are a number of drawbacks with currently available methods for treating eye disorders and diseases. For example, in the case of these posterior segment eye diseases, traditional routes of drug administration such as topical or oral dosing often fall short of reaching the disease site. As a result, current methods for treating back-of-the-eye diseases involve introducing drugs directly into the vitreous chamber of the eye via intraocular injections or intravitreal implants. The eye's natural circulatory processes rapidly remove solutions that are injected directly into the vitreous chamber. Subsequently, this approach often requires frequent, large dose injections which have been associated with complications such as glaucoma and cataract formation. Furthermore, large molecular weight molecules (>70 kD) are virtually incapable of traversing the tight junction complexes of the retinal pigment epithelium and retinal capillaries. Microparticle injections have improved the sustained release capabilities of conventional injections, but this still does not resolve the widespread distribution of the medication via intraocular convection. In the case of steroids, this distribution is known to lead to adverse effects such as glaucoma and cataract. Additionally, the eye's natural circulatory processes have a subtle anterior to posterior ocular convection, which results in lower drug concentrations at the back of the eye where the disease is developing.

It thus would be desirable to provide safe and effective methods for treating an eye, particularly treating "retinal and/or choroidal disorders or diseases, by delivering a therapeutic medium directly to the desired treatment site. In particular, it would be desirable to provide localized sustained delivery of a therapeutic medium at the retina and/or the choroid while minimizing such action in other tissues of the eye. It would be desirable to provide a method that minimizes trauma and eliminates the need for fluid dissection of the retina. It would further be desirable to provide a method that effectively lowers the dosage of therapeutics required for treatment. It would further be desirable to provide a method that reduces and even eliminates the side effects associated with intravitreal delivery of therapeutics. It would further be desirable to provide a method that effectively and efficiently delivers large molecular weight drugs and proteins to a treatment site.

SUMMARY OF THE INVENTION

One aspect the present invention provides sustained release implants for delivering one or more bioactive agents subretinally to the eye of a mammal. Implants of the invention comprise one or more solid biocompatible polymers and one or more bioactive agents. The implants deliver the one or more bioactive agents subretinally in an amount that is substantially less than the amount delivered by systemic, topical, and whole organ delivery systems in order to achieve the same therapeutic effect.

In some embodiments, the polymer matrix and the one or more bioactive agents, alone, form the implant. In other embodiments, the implant comprises a biocompatible core having an outer surface that is at least partially covered with a coating layer that comprises a biocompatible polymer matrix and one or more bioactive agents. In some embodiments, the coating layer covers the entire outer surface of the core. In other embodiments, the coating layer covers one or more portions of the outer surface of the core, leaving one or more portions of the outer surface of the core uncoated. In some embodiments the coating layer is tapered or feathered at one or at both of its ends. In some embodiments at least the distal and proximal ends of the core are covered with coating layers and the coating layers are tapered or feathered.

Polymers useful in a polymer matrix of an implant are biocompatible polymers and may be biostable (i.e., non-biodegradable) or biodegradable. Examples of biostable polymers include polyurethanes, silicones, polyesters, polyolefins (e.g., polyethylene or polypropylene), polyisobutylene, acrylic polymers, vinyl halide polymers, polyvinyl ethers, polyvinyl methyl ether, polyvinylidene halides, polyacrylonitrile, polyvinyl ketones, polyvinyl aromatics, polyvinyl esters (e.g., poly(alkyl(meth)acrylates) such as poly((methyl) methacrylate) or poly((butyl)methacrylate)), polyvinyl amides, polyamides, polycaprolactam, polycarbonates, polyoxymethylenes, polyimides, polyethers, polyurethanes, rayon, rayon-triacetate, cellulose acetate, cellulose butyrate, cellophane, cellulose nitrate, cellulose propionate, cellulose ethers, carboxymethyl cellulose and copolymers (e.g., polyethylene vinyl acetate) and blends of the above polymers. Examples of biodegradable polymers include poly(L-lactic acid), poly(caprolactone), poly(lactide-co-glycolide), poly (hydroxybutyrate), poly(hydroxybutyrate-co valerate), polydioxanone, polyorthoesters, polyanhydrides, poly(glycolic acid), poly(D,L lactic acid), poly(glycolic acid-co-trimethylene carbonate), poly(phosphate esters), polyphosphoester urethanes, poly(amino acids), cyanoacrylates, poly(trimethylene carbonates), polycarbonates, poly(iminocarbonates), polyesters, copoly(ether-esters), polyalkylene oxalates, polyphosphazenes and copolymers and blends of the above polymers. Biodegradable materials such as fibrin, fibrinogen, cellulose, dextrans, polysaccharides, starch collagen, chromic gut, and hyaluronic acid may also be used.

Non-polymer biocompatible materials may also form the core of an implant of the invention. Examples include titanium-nickel alloy wire, titanium alloys, nickel-cobalt base alloys, stainless steel, cobalt-chromium alloys, and biodegradable magnesium alloys. In an exemplary embodiment, the core is titanium nickel wire having the smallest commercially available diameter (e.g., about 10 μm to about 200 μm), thereby maximizing the amount of bioactive agent that the implant may contain. In some embodiments, the core material and core thickness are selected to provide the implant with the desired rigidity and flexibility.

In some embodiments, the outer surface area of the implant core is partially or completely covered with a coating layer comprising a biocompatible polymer matrix and one or more bioactive agents and the coating layer is partially or totally covered with one or more additional coating layers comprising one or more biocompatible polymer that modify the release rate characteristics (e.g., elution rate) of the one or more bioactive agents. Examples of biocompatible polymers that may be used for the additional coating layer include poly(caprolactone), poly(methylmethacrylate), polyesters, chromic gut, polyorthoesters, polypropylene, polyethylene vinyl acetate or poly(butylmethacrylate). In an exemplary embodiment, the coating layer comprises poly(caprolactone).

In some embodiments, the outer surface of the core is coated along a portion of its length with a coating layer comprising a biocompatible polymer matrix and one or more bioactive agents and the implant additionally includes an uncoated length of core that provides a handling portion (e.g., uncoated regions of about 10 mm in length, or less) by which the implant may be grasped, docked with a surgical instrument, or used for easy device retrieval after a period of implantation in the eye.

Examples of bioactive agents that may be delivered by implants of the invention include drugs, medicaments, antibiotics, antibacterials, antiproliferatives, neuroprotectives, anti-inflammatories (steroidal and non-steroidal), growth factors, neurotropic factors, antiangiogenics, thrombolytics or genes. More specifically, the one or more bioactive agents may be selected from thrombin inhibitors; anti thrombogenic agents; thrombolytic agents; fibrinolytic agents; vasospasm inhibitors; calcium channel blockers; vasodilators; antihypertensive agents; antimicrobial agents, antifungals, and antivirals; inhibitors of surface glycoprotein receptors; antiplatelet agents; antimitotics; microtubule inhibitors; anti-secretory agents; active inhibitors; remodeling inhibitors; antisense nucleotides; anti-metabolites; antiproliferatives, including antiangiogenesis agents; anticancer chemotherapeutic agents; anti-inflammatories; non-steroidal anti-inflammatories; antiallergenics; anti-proliferative agents; decongestants;

miotics and anti-cholinesterase; antineoplastics; immunological drugs; hormonal agents; immunosuppressive agents, growth hormone antagonists, growth factors; inhibitors of angiogenesis; dopamine agonists; radiotherapeutic agents; peptides; proteins; enzymes; extracellular matrix components; ACE inhibitors; free radical scavengers; chelators; antioxidants; anti-polymerases; photodynamic therapy agents; gene therapy agents; and other therapeutic agents such as prostaglandins, antiprostaglandins, prostaglandin precursors, and combinations thereof. In an exemplary embodiment, the implant comprises corticosteroid triamcinolone acetonide in a polymer matrix comprising biodegradable poly(caprolactone).

Implants of the invention are typically designed to minimize interference with the functions of the eye and discomfort and damage to the eye. In some embodiments, the implant is rod-like or filament-like in shape. In some embodiments, the implant may have a distal end that is beveled, tapered, or sharpened. Alternatively, the implant may have a distal end that is blunt or rounded.

In some embodiments, the implant has a total diameter that is no greater than about 1000 µm, in other embodiments no greater than about 900 µm, in other embodiments no greater than about 800 µm, in other embodiments no greater than about 700 µm, in other embodiments no greater than about 600 µm, in other embodiments no greater than about 500 µm, in other embodiments no greater than about 400 µm, in other embodiments no greater than about 300 µm, in other embodiments no greater than about 200 µm, in other embodiments no greater than about 100 µm, in other embodiments no greater than about 50 µm. In some embodiments, the total diameter of the implant ranges from about 200 µm to about 500 µm.

In some embodiments, the implants of the invention have a length that is no greater than about 5 mm, in other embodiments no greater than about 4.5 mm, in other embodiments no greater than about 4 mm, in other embodiments no greater than about 3.5 mm, in other embodiments no greater than about 3.0 mm, in other embodiments no greater than about 2.9 mm, in other embodiments no greater than about 2.8 mm, in other embodiments no greater than about 2.7 mm, in other embodiments no greater than about 2.6 mm, in other embodiments no greater than about 2.5 mm, in other embodiments no greater than about 2.4 mm, in other embodiments no greater than about 2.3 mm, in other embodiments no greater than about 2.2 mm, in other embodiments no greater than about 2.1 mm, in other embodiments no greater than about 2 mm. In some embodiments, the length of the implant ranges from about 2.25 mm to about 2.75 mm.

In some embodiments, the implants of the invention have a bioactive agent elution rate of at least about 0.0001 µg per day, in other embodiments at least about 0.001 µg per day, in other embodiments at least about 0.01 µg per day, in other embodiments at least about 0.1 µg per day, in other embodiments at least about 1 µg per day, in other embodiments at least about 10 µg per day, in other embodiments at least about 100 µg per day, and in other embodiments at least about 1000 µg per day.

In some embodiments, the implants of the invention are capable of delivering about 2 to about 1,000,000 times less bioactive agent than whole organ delivery systems deliver in order to achieve the same therapeutic effect. Further, in some embodiments, the implants are capable of delivering about 2 to about 1,000,000 times less bioactive agent than systemic or topical delivery systems deliver in order to achieve the same therapeutic effect.

In some embodiments, the implants of the invention provide a therapeutic effect by eluting one or more bioactive agents at no more than about 90% excess bioactive agent than that required to provide a therapeutic affect, in other embodiments at no more than about 80% excess, in other embodiments at no more than about 70% excess, in other embodiments at no more than about 60% excess, in other embodiments at no more than about 50% excess, in other embodiments at no more than about 40% excess, in other embodiments at no more than about 30% excess, in other embodiments at no more than about 20% excess, in other embodiments at no more than about 10% excess, in other embodiments at no more than about 5% excess, in other embodiments at no more than about 1% excess bioactive agent than that required to provide a therapeutic affect.

In another aspect, the invention provides a method of fabricating an implant for the sustained delivery of at least one bioactive agent to the eye, wherein the device is implanted subretinally, comprising: using low temperature process to form the implant by combining one or more polymers with one or more bioactive agents, wherein the implant is fabricated such that the one or more bioactive agents are delivered at a dose substantially the same as the dose required to provide a therapeutic effect.

In some embodiments the method comprises the steps of: (a) dissolving one or more polymers in a solvent to form a complex fluid; (b) adding at least one bioactive agent to the complex fluid to produce a homogeneous solution of the one or more bioactive agents and/or a solution with a dispersed phase of the one or more bioactive agents; (c) optionally drying the solution to a solid form; (d) optionally heating the solid form to a temperature just below the melting point of the polymer(s); and (e) forming the implant device out of the solution of (b) or the solid form of (c). In some embodiments the complex fluid is dried to a solid form. In these embodiments, the solid form is typically heated to a temperature just below the melting point of the polymer(s) during the forming step (i.e., step (e)). For example, the process may be carried out at a temperature of no greater than about 100° C. In some embodiments, the step of forming the implant device is carried out by melt-extrusion-drawing. In other embodiments the solution of step (b) is not dried to a solid form. In these embodiments, heating may not be required during the forming step (i.e., step (e)) because of the presence of solvent in the solution. Representative solvents include chloroform, THF, or any other organic hydrocarbon having a suitable solubility parameter.

In another aspect, the invention provides methods for administering a bioactive agent to the posterior segment of an eye by inserting an implant of the invention within the eye and allowing one or more bioactive agents to be delivered. In another aspect, the invention provides methods for the treatment and/or prevention of disorders and or diseases of the eye, comprising implanting the device in accordance with the present invention within the eye; and allowing one or more bioactive agents to be delivered to the desired retinal treatment site.

In some embodiments the implant is positioned in one or more tissue layers above the choroid but below the nerve fiber layer. In some embodiments, two or more implants are subretinally implanted in the eye so that the two or more implants simultaneously elute one or more bioactive agents to one or more treatment sites.

In some embodiments, the implant is capable of piercing and/or penetrating the eye structure to achieve implantation within the eye. For example, the implant may have a beveled, tapered or sharpened distal end to facilitate piercing or penetration. In some embodiments, an instrument is used to insert the implant within the eye. In some embodiments, the implants include one or more uncoated portions which may be grasped or docked with a surgical instrument to insert the implant within the eye.

In some embodiments of the invention, the implant is inserted within the eye to provide a particular concentration of bioactive agent for delivery based on the distance between the implant, or even the number of implants, and the tissue regions or layers to be treated.

In some embodiments, it may be desirable to administer a viscous fluid, hydrogel or other solid or semi-solid material into the subretinal space to create the space where the implant will reside.

According to the present invention, one or more bioactive agents are delivered substantially only to the portion of the eye being treated (i.e., the treatment site). In some embodiments, at least 5% of the bioactive agent that is eluted by the implant is delivered to the portion of the eye being treated, in other embodiments at least 10%, in other embodiments at least 20%, in other embodiments at least 30%, in other embodiments at least 40%, in other embodiments at least 50%, in other embodiments at least 60%, in other embodiments at least 70%, in other embodiments at least 80%, and in other embodiments at least 90%.

Further, the implants and methods of the present invention are capable of delivering one or more bioactive agents such that no significant amount of the one or more bioactive agents is delivered to healthy tissues. In some embodiments, less than 95% of one or more bioactive agents eluted by the implant is delivered to healthy tissues, in other embodiments less than 90%, in other embodiments less than 80%, in other embodiments less than 70%, in other embodiments less than 60%, in other embodiments less than 50%, in other embodiments less than 40%, in other embodiments less than 30%, in other embodiments less than 20%, in other embodiments less than 10%, and in other embodiments less than 5% is delivered to healthy tissue.

The present invention provides a direct approach for delivering one or more bioactive agents to a treatment site, thereby reducing the required dosage for effective treatment. Further, such methods may reduce the side effects associated with intravitreal delivery of bioactive agents. The present methods further provide an improved route for the delivery of large molecular weight drugs and proteins to a treatment site.

Other aspects, embodiments, and advantages of the invention will become readily apparent to those skilled in the art are discussed below. As will be realized, the invention is capable of other and different embodiments without departing from the invention. Thus the following description as well as any drawings appended hereto shall be regarded as being illustrative in nature and not restrictive.

The instant invention is most clearly understood with reference to the following definitions:

As used herein:

"Aqueous" of the eye shall be understood to mean the aqueous humor of the eye.

"Biocompatible" refers to the ability of a material to be accepted by and to function in a recipient without eliciting a significant foreign body response (such as, for example, an immune, inflammatory, thrombogenic, or the like response). For example, when used with reference to one or more of the polymeric matrix materials of the invention, biocompatible refers to the ability of the polymeric matrix material (or polymeric matrix materials) to be accepted by and to function in its intended manner in a recipient. Accordingly, an implant can be characterized as "biocompatible" if it is capable of functioning or existing in contact with biological fluid and/or tissue of a living organism with a net beneficial effect on the living organism.

"Complex fluid" shall be understood to mean a polymeric liquid or melt that is in a fluid state through chemical and/or thermal thermodynamic mechanisms; possesses a molecular or structural length scales component phase much larger than atomic and may include additional component phases such as stabilizers, solvents, additives and even therapeutics. While in this fluid state, this "complex fluid" is further characterized by complex pseudoplastic, Newtonian or non-Newtonian rheology.

"Organ" shall be understood to mean a collection of tissues that function cooperatively to provide a specific function. For example, a collection of tissues such as the retina, choroid, lens and other related structure that makes up the visual organ.

"Surgical bleb" shall be understood to mean a local retinal fluid detachment created by a small gauge needle syringe or injection system.

"Sustained release implant" shall be understood to mean any of a number of implants that are configured and arranged to release one or more bioactive agents over an extended period of time in a controlled fashion.

"Subretinal space" shall be understood to mean the space between the retinal pigment epithelium cells and the photoreceptors cells of the eye.

"Therapeutically effective amount" refers to that amount of a bioactive agent alone, or together with other substances, that produces the desired effect (such as treatment of a medical condition such as a disease or the like, or alleviation of pain) in a patient. During treatment, such amounts will depend upon such factors as the particular condition being treated, the severity of the condition, the individual patient parameters including age, physical condition, size and weight, the duration of the treatment, the nature of the particular bioactive agent thereof employed and the concurrent therapy (if any), and like factors within the knowledge and expertise of the health practitioner. A physician or veterinarian of ordinary skill can readily determine and prescribe the effective amount of the bioactive agent required to treat and/or prevent the progress of the condition.

"Vitreous" shall be understood to mean the vitreous or vitreal cavity of a mammalian eye.

BRIEF DESCRIPTION OF THE DRAWINGS

For a fuller understanding of the nature and desired objects of the present invention, reference is made to the following detailed description taken in conjunction with the accompanying drawing figures wherein like reference character denote corresponding parts throughout the several views and wherein.

DETAILED DESCRIPTION OF THE INVENTION

The embodiments of the present invention described below are not intended to be exhaustive or to limit the invention to the precise forms disclosed in the following detailed description. Rather, the embodiments are chosen and described so that others skilled in the art can appreciate and understand the principles and practices of the present invention.

The invention provides subretinal drug delivery systems for providing sustained delivery of one or more bioactive agents within the subretinal space of a mammal, and methods for administering or delivering the bioactive agents within the subretinal space of a mammal using such delivery systems. The invention also provides methods for fabricating the delivery systems, in particular, methods for fabricating implants that are used to deliver the one or more bioactive agents. The drug delivery systems and methods overcome limitations of current devices and treatment methods for retinal disease.

In embodiments of the invention, the subretinal drug delivery system comprises implants that can be placed within the eye at a desired treatment location. In particular, the implant comprises a biocompatible polymer matrix including one or more bioactive agents. In some embodiments the biocompatible polymer matrix of the implant is biodegradable or bioabsorbable.

Figure 14:
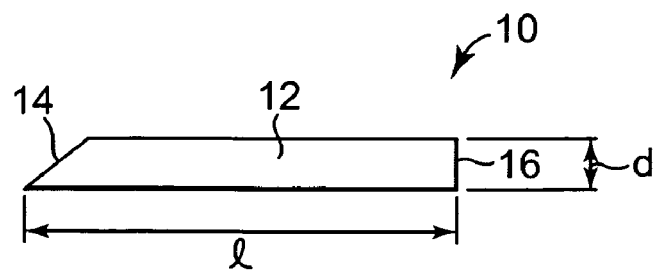
FIG. 14 shows a representative illustration of a subretinal implant in accordance with one embodiment of the present invention.

In one embodiment, a polymer matrix containing one or more bioactive agents alone forms an implant. It is to be understood that this means that the polymer matrix with the one or more bioactive agents form substantially all of the implant, but that other small amounts of materials may also be contained in the implant due to processing and stabilizing techniques used in forming the implant. Referring to FIG. 14, implant 10 comprises polymer matrix 12 containing one or more bioactive agents. Implant 10 has length "l" and diameter "d" as shown in FIG. 14. Implant 10 has distal end 14 and proximal end 16. The distal or proximal ends (or both) of the implant may be tapered, rounded, beveled, blunt, or may have other desirable end shapes. In the embodiment of FIG. 14, implant 10 has a beveled distal end 14 and has a blunt proximal end 16.

Figure 10:
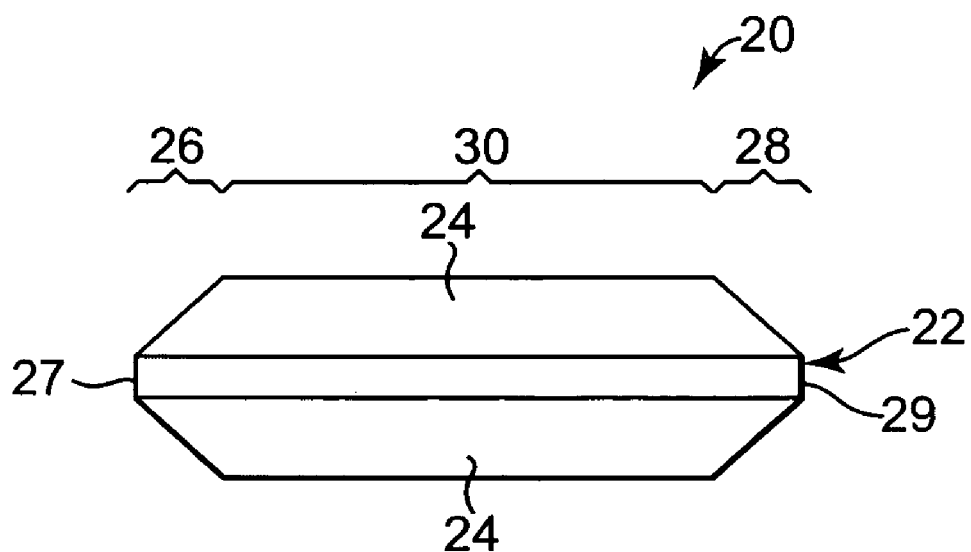
FIG. 10 shows a representative longitudinal cross-sectional view of the subretinal implant of FIG. 11.
Figure 11:
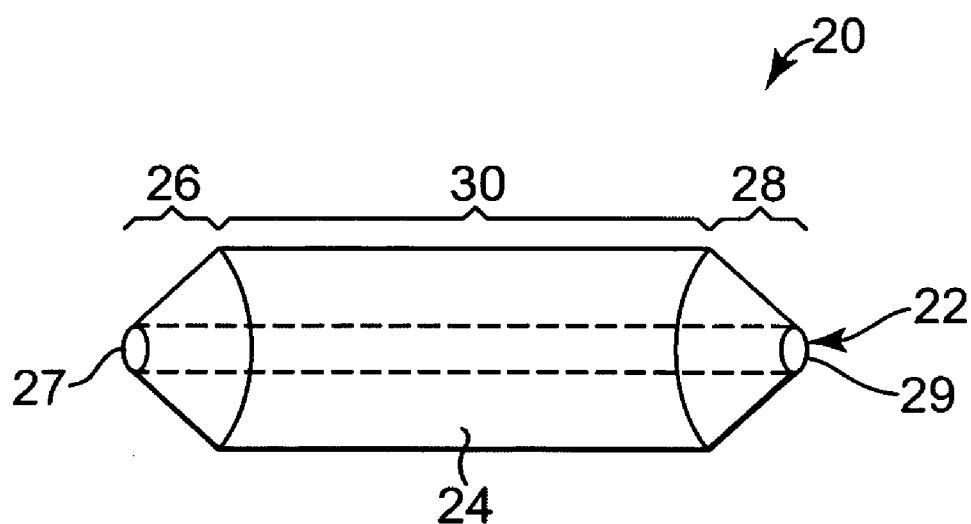
FIG. 11 shows a representative illustration of a side view of a subretinal implant in accordance with one embodiment of the present invention.

In another embodiment, the implant comprises a biocompatible core that is coated with a coating layer of a polymer matrix-bioactive material (i.e., a polymer matrix including one or more bioactive agents). Referring to FIGS. 10-11, one embodiment of an implant of the type that has a core is shown. Implant 20 includes core 22, having proximal end 27 and distal end 29, and coating layer 24 comprising polymer matrix-bioactive material. In the embodiment of FIGS. 10-11, the coating layer 24 of polymer matrix-bioactive material is coated over the entire length of core 22. The coating layer 24 of polymer matrix-bioactive material includes proximal transition segment 26, distal transition segment 28, and center portion 30. In this embodiment, proximal transition segment 26 and distal transition segment 28 have been feathered (i.e., a sloped transition segment).

Figure 12:
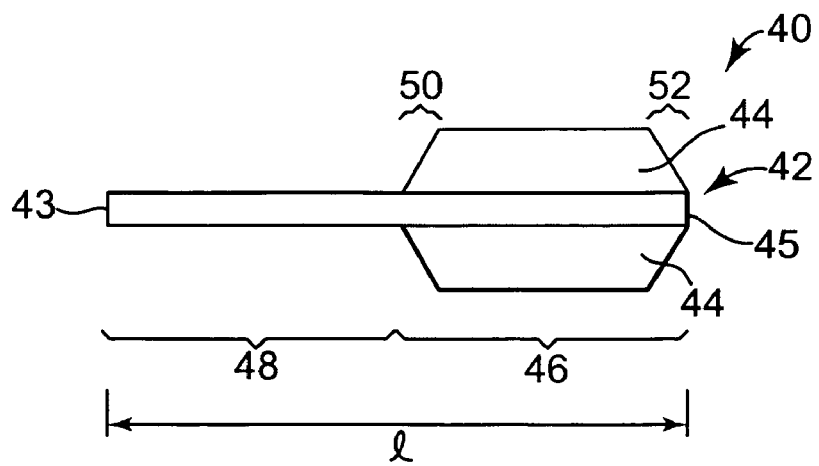
FIG. 12 shows a representative longitudinal cross-sectional view of the subretinal implant of FIG. 13.
Figure 13:
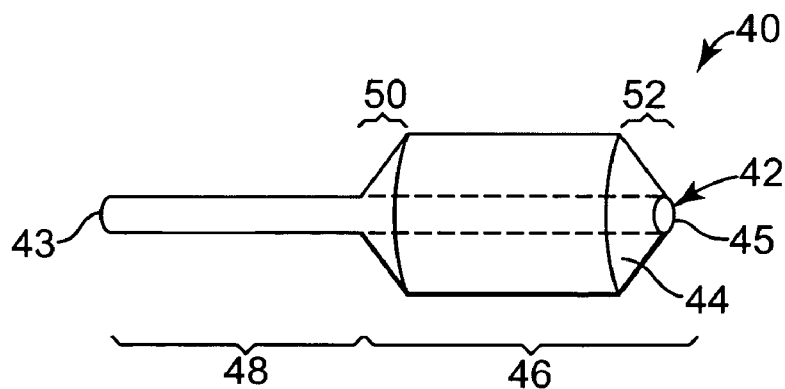
FIG. 13 shows a representative illustration of a side view of a subretinal implant in accordance with one embodiment of the present invention.

In another embodiment, as shown in FIGS. 12-13, implant 40 includes core 42, having proximal end 43 and distal end 45. A coating layer 44 of polymer matrix-bioactive material is coated over a portion of the length "l" of core 42, resulting in coated portion 46 and uncoated portion 48. The uncoated portion 48 may be useful to provide a handling portion by which the implant may be grasped or docked with a surgical instrument (e.g. by microsurgical instruments) to prevent any potential damage to the coating layer 44 upon handling. In one embodiment, the uncoated portion of the implant device could be left periretinal for easy retrieval in follow-up surgery. In the embodiment of FIGS. 12-13, proximal transition segment 50 and distal transition segment 52 of coated portion 46 have been feathered (i.e., a sloped transition segment). Without being bound by theory, it is believed that feathering the distal and proximal ends of the implant may enhance the uniformity, processing reproducibility, and ease of implantation.

The size, geometry and materials used in forming the core can be selected to provide the desired characteristics. For example, thinner cores may be used to provide less rigidity and to allow for thicker coating layers, thereby maximizing the volume of bioactive agent in the implant. Further, the material forming the core can be selected to provide the desired rigidity or flexibility. Still further, the core material may be selected so as to facilitate the ability of the coating layer to adhere to the core. Additionally, the the surface of the core may be primed, roughened, or chemically modified to further improve adhesion of the polymer layer to the core.

In some embodiments, the implant can further include a layer of polymer material that modifies the bioactive agent release rate characteristics. For example, a thin layer of poly (caprolactone) can be coated on the implant. Such a poly (caprolactone) layer can also provide a degradation rate-controlling barrier, protection of the bioactive agent from environmental degradation prior to implantation, or may delay the time point of release of the drug.

Biocompatible polymers useful in the polymer matrix may be biostable (i.e., non-biodegradable) or biodegradable. Examples of biostable polymers include polyurethanes, silicones, polyesters, polyolefins (e.g., polyethylene or polypropylene), polyisobutylene, acrylic polymers, vinyl halide polymers, polyvinyl ethers, polyvinyl methyl ether, polyvinylidene halides, polyacrylonitrile, polyvinyl ketones, polyvinyl aromatics, polyvinyl esters (e.g., poly(alkyl(meth)acrylates) such as poly((methyl)methacrylate) or poly((butyl)methacrylate)), polyvinyl amides, polyamides, polycaprolactam, polycarbonates, polyoxymethylenes, polyimides, polyethers, polyurethanes, rayon, rayon-triacetate, cellulose acetate, cellulose butyrate, cellophane, cellulose nitrate, cellulose propionate, cellulose ethers, carboxymethyl cellulose and copolymers (e.g., polyethylene vinyl acetate) and blends of the above polymers.

Examples of biodegradable polymers include poly(L-lactic acid), poly(caprolactone), poly(lactide-co-glycolide), poly(hydroxybutyrate), poly(hydroxybutyrate-co valerate), polydioxanone, polyorthoesters, polyanhydrides, poly(glycolic acid), poly(D,L lactic acid), poly(glycolic acid-co-trimethylene carbonate), poly(phosphate esters), polyphosphoester urethanes, poly(amino acids), cyanoacrylates, poly (trimethylene carbonates), polycarbonates, poly (iminocarbonates), polyesters, copoly(ether-esters), polyalkylene oxalates, polyphosphazenes and copolymers and blends of the above polymers. Biodegradable materials such as fibrin, fibrinogen, cellulose, dextrans, polysaccharides, starch collagen, chromic gut, and hyaluronic acid could also be used.

Selection of the polymers may depend, for example, on the desired properties of the implant including, for example, the bioactive agents that are to be delivered by the implant and the rate of delivery and duration of delivery of the bioactive agents.

In some embodiments, the biocompatible polymer comprises, in whole or in part, repeating caprolactone monomer units (e.g., poly(caprolactone) or co-polymers thereof). It has been found that poly(caprolactone) is well tolerated by the retinal tissue and can deliver bioactive agents without eliciting inflammatory response or complications. For example, in the embodiment of FIGS. 4-6, poly(caprolactone) can elute steroid for a period of at least 4 weeks without eliciting inflammatory response or complications. Thus, in one embodiment, the implant is formed using a biodegradable poly(caprolactone) polymer matrix. In one embodiment, the implant is rod-shaped and includes corticosteroid triamcinolone acetonide in a biodegradable poly(caprolactone) polymer matrix. Such embodiments may optionally include a core.

In some embodiments, the biocompatible polymer comprises (a) a first polymer selected from poly(alkyl(meth)acrylates), aromatic poly(meth)acrylates, and mixtures thereof; and (b) a second polymer comprising a poly(ethylene-co-vinyl acetate) copolymer. Suitable first polymers and second polymers can be prepared using conventional organic synthesis procedures and/or are commercially available from a variety of sources. Preferably, such polymers are either provided in a form suitable for in vivo use in a coating composition, or are purified for such use to a desired extent (for example, by removing impurities) by conventional methods available to those skilled in the art.

Preferably, the first polymer provides one or more desirable properties, such as compatibility with the second polymer and bioactive agent(s), hydrophobicity, durability, bioactive agent release characteristics, biocompatibility, molecular weight, and commercial availability. Preferably, the first polymer comprises poly(alkyl(meth)acrylate), aromatic poly(meth)acrylate, or a combination of poly(alkyl(meth)acrylate) and aromatic poly(meth)acrylate.

An example of a suitable poly(alkyl(meth)acrylate) includes poly(n-butylmethacrylate). In one preferred embodiment, the polymeric coating composition comprises poly(n-butylmethacrylate) ("pBMA") and poly(ethylene-co-vinyl acetate) copolymers as the second polymer ("pEVA"). This composition has proven useful with absolute polymer concentrations in the range of about 0.05% to about 70% by weight of the coating composition. As used herein "absolute polymer concentration" refers to the total combined concentrations of first polymer and second polymer in the coating composition. In one embodiment, the coating composition comprises poly(alkyl(meth)acrylate) (e.g., such as poly(n-butylmethacrylate)) with a weight average molecular weight in the range of about 100 kilodaltons (kD) to about 1000 kD, and a pEVA copolymer with a vinyl acetate content in the range of about 10% to about 90% by weight of the pEVA copolymer. In another embodiment, the polymer composition comprises poly(alkyl(meth)acrylate) (e.g., such as poly(n-butylmethacrylate)) with a molecular weight in the range of about 200 kD to about 500 kD, and a pEVA copolymer with a vinyl acetate content in the range of about 30% to about 34% by weight. The concentration of the bioactive agent(s) in the polymeric coating composition of this embodiment can be in the range of about 0.01% to about 90% by weight, based upon the weight of the final coating composition.

As used herein "weight average molecular weight" or $M_w$, is an absolute method of measuring molecular weight and is particularly useful for measuring the molecular weight of a polymer preparation. The weight average molecular weight ($M_w$) can be defined by the following formula:

$$M_w = \frac{\sum N_i M_i^2}{\sum N_i M_i}$$

wherein N represents the number of moles of a polymer in the sample with a mass of M, and $\Sigma_i$ is the sum of all $N_i M_i$ (species) in a preparation. The $M_w$ can be measured using common techniques, such as light scattering or ultracentrifugation. Discussion of $M_w$ and other terms used to define the molecular weight of polymer preparations can be found in, for example, Allcock, H. R. and Lampe, F. W., *Contemporary Polymer Chemistry*; pg 271 (1990).

Coating compositions including aromatic poly(meth)acrylates can provide unexpected advantages in certain embodiments. Such advantages relate, for instance, to the ability to provide coatings having different characteristics (such as different solubility characteristics) than other coatings (e.g., those that include a poly(alkyl(meth)acrylate) polymer), while maintaining a desired combination of other properties. Without intending to be bound by a particular theory, it appears that the increased solubility (particularly in more polar solvents) that is provided by an aromatic, rather than an alkyl poly(meth)acrylate of this invention, permits the use of poly(ethylene-co-vinyl acetate) polymers that are themselves more polar (e.g., having significantly greater vinyl acetate concentrations) than those typically preferred for use with the poly(alkyl(meth)acrylates).

Examples of suitable aromatic poly(meth)acrylates include poly(aryl(meth)acrylates), poly(aralkyl(meth)acrylates), and poly(aryloxyalkyl(meth)acrylates), in particular those with aryl groups having from six to sixteen carbon atoms and weight average molecular weights in the range of about 50 kD to about 900 kD. Preferred aromatic poly(meth)acrylates include those compounds wherein at least one carbon chain and at least one aromatic ring are combined with acrylic groups (typically esters). For example, a poly(aralkyl (meth)acrylate) or poly(arylalkyl(meth)acrylate) can be made from aromatic esters derived from alcohols also containing aromatic moieties.

Examples of poly(aryl(meth)acrylates) include poly(9-anthracenylmethacrylate), poly(chlorophenylacrylate), poly (methacryloxy-2-hydroxybenzophenone), poly(methacryloxybenzotriazole), poly(naphthylacrylate), poly (napthylmethacrylate), poly(4-nitrophenylacrylate), poly (pentachlorophenylacrylate), poly (pentabromophenylacrylate), poly (pentafluorophenylacrylate), poly (pentachlorophenylmethacrylate), poly (pentabromophenylmethacrylate), poly(pentafluorophenylmethacrylate), poly(phenylacrylate), and poly(phenylmethacrylate).

Examples of poly(aralkyl(meth)acrylates) include poly (benzylacrylate), poly(benzylmethacrylate), poly(2-phenethylacrylate), poly(2-phenethylmethacrylate), and poly(1-pyrenylmethylmethacrylate).

Examples of poly(aryloxyalkyl(meth)acrylates) include poly(phenoxyethylacrylate), poly(phenoxyethylmethacrylate), poly(ethyleneglycolphenyletheracrylates), and poly (ethyleneglycolphenylether methacrylates) with varying polyethyleneglycol molecular weights.

The second polymer of the polymeric coating composition preferably provides one or more desirable properties, such as compatibility with the first polymer and bioactive agent, hydrophobicity, durability, bioactive agent release characteristics, biocompatibility, molecular weight, and commercial availability, particularly when used in admixture with the first polymer.

Examples of suitable second polymers are commercially available and include poly(ethylene-co-vinyl acetate) having vinyl acetate concentrations in the range of about 10% to about 90% by weight of the pEVA copolymer, or in the range of about 20% to about 60% by weight of the pEVA copolymer, or in the range of about 30% to about 34% by weight of the pEVA copolymer. Poly(ethylene-co-vinyl acetate) co-polymers having lower percent vinyl acetate can become increasingly insoluble in typical solvents, such as THF, toluene, and the like. The second polymer can be obtained commercially in the form of beads, pellets, granules, and the like.

For application to the outer surface of a core, a coating composition may comprise a solvent, a first polymer and second polymer dissolved in the solvent, and one or more bioactive agents dispersed in the polymer/solvent solution. The solvent is preferably one in which the polymers form a true solution. The one or more bioactive agents can either be soluble in the solvent or may form a dispersion in the solvent. In use, these embodiments do not require any mixing on the part of the user prior to application of the coating composition to the device. In some embodiments, the coating composition can provide a one-part system that can be applied to the device in one composition. For example, U.S. Pat. No. 6,214,901 exemplifies the use of tetrahydrofuran (THF) as a solvent. While THF is suitable, and at times preferred for certain coating compositions, other solvents can be used in accordance with the invention as well, including, for example, alcohols (e.g., methanol, butanol, propanol, isopropanol, and the like), alkanes (e.g., halogenated or unhalogenated alkanes such as hexane and cyclohexane), amides (e.g., dimethylformamide), ethers (e.g., dioxolane), ketones (e.g., methylketone), aromatic compounds (e.g., toluene and xylene), acetonitrile, and esters (e.g., ethyl acetate).

The coating layer formed from the coating composition is biocompatible. In addition, the layer is preferably useful under a broad spectrum of both absolute concentrations and relative concentrations of the polymers. The physical properties of the coating layer (such as tenacity, durability, flexibility and expandability) will typically be suitable over a broad range of polymer concentrations. Furthermore, the ability to control the release rates of a variety of bioactive agents can preferably be manipulated by varying the absolute and/or relative concentrations of the polymers and/or the bioactive agent(s).

In some embodiments the polymer matrix comprises a biodegradable composition comprising a blend of a first polymer and a second polymer. Such blends are described in U.S. patent application Ser. No. 11/317,212 entitled "Biodegradable Coating Compositions Comprising Blends", filed Dec. 22, 2005. The reported biodegradable compositions comprise blends of: (a) a first biodegradable polymer that is a copolymer of polyalkylene glycol terephthalate and an aromatic polyester; and (b) a second biodegradable polymer. The second biodegradable polymer is selected to have a slower bioactive agent release rate relative to the first biodegradable polymer.

In some embodiments, the polyalkylene glycol terephthalate is selected from the group of polyethylene glycol terephthalate, polypropylene glycol terephthalate, polybutylene glycol terephthalate, and combinations of these. In some embodiments, the polyester is selected from polyethylene terephthalate, polypropylene terephthalate, polybutylene terephthalate, and combinations of these. For example, the first polymer may be a copolymer of polyethylene glycol terephthalate and polybutylene terephthalate in relative amounts of 70-80% polyethylene glycol terephthalate and 5-20% polybutylene terephthalate.

The second biodegradable polymer comprises a polymer derived from monomers selected from lactic acid, glycolic acid, caprolactone, ethylene glycol, and ethyloxyphosphate. For example, the second biodegradable polymer may comprises a blend of two or more poly(ester-amide) polymers. In some embodiments, the second biodegradable polymer is more hydrophobic relative to the first biodegradable polymer.

In some embodiments, the polymer matrix comprises a biodegradable or bioresorbable material such as the materials described in International Publication No. WO 2006/023130 entitled "Biodegradable Controlled Release Bioactive Agent Delivery Device". This application describes various biodegradable polymers, including species of polycarbonates, that can be utilized as a polymer matrix in accordance with the invention. In some embodiments, the biodegradable materials comprises a random block copolymer having the formula:

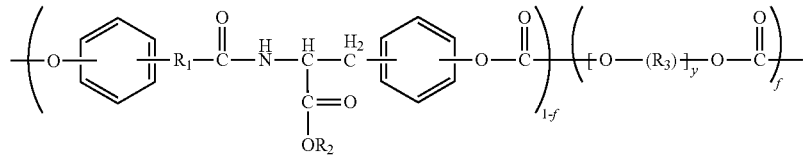

wherein $R_1$ is —CH=CH— or (—$CH_2$—)$_j$, in which j is zero or an integer from one to eight;

$R_2$ is selected from straight and branched alkyl and alkylaryl groups (e.g., straight-chained alkyl group selected from ethyl, butyl, hexyl, and octyl groups.) containing up to 18 carbon atoms and optionally containing at least one ether linkage, and derivatives of biologically or pharmaceutically active compounds covalently bonded to the copolymer;

each $R_3$ is independently selected from alkylene groups containing 1 to 4 carbon atoms (e.g., ethylene);

y is between 5 and about 3000 (e.g., 20 to 200); and f is the percent molar fraction of alkylene oxide in the copolymer, and is in the range of about 1 to about 99 mole percent (e.g., 5 to 95 mole percent).

In some embodiments, the polymer matrix comprises a hydrogel. Examples of hydrogels include the dextran based hydrogels described in WO 02/17884 (Hennink et al.)

In some embodiments, non-polymer biocompatible materials form the core of an implant of the invention. Examples include include titanium-nickel alloy wire (e.g., Nitinol wire, commercially available from Nitinol Devices and Components, Freemont Calif.), titanium alloys, nickel-cobalt base alloys, stainless steel, cobalt-chromium alloys, and biodegradable magnesium alloys. It is to be understood that the core material is not limited to the examples provided herein and can be any conventional material used in implant devices.

The cross-sectional shape of the core of an implant may be any desired shape, but is typically circular. The maximum cross-section dimension (e.g., diameter) of the core is typically less than about 200 μm, in some embodiments about 10 μm to about 200 μm. In an exemplary embodiment, the core comprises titanium-nickel wire. In a specific embodiment, the core is titanium-nickel wire having a diameter of 80 μm or less, thereby maximizing the volume of bioactive agent that can be loaded, while still providing a structure for the implant.

In another aspect, the invention provides methods for preparing an implantable device. In some embodiments the method comprises the steps of: (a) dissolving one or more polymers in a solvent to form a complex fluid; (b) adding at least one bioactive agent to the complex fluid to produce a homogeneous solution of the one or more bioactive agents and/or a solution with a dispersed phase of one or more bioactive agents; (c) optionally drying the complex fluid to a solid form; (d) optionally heating the solid form to a temperature just below the melting point of the polymer(s); and (e) forming the implant device out of the solution of (b) or the solid form of (c).

In some embodiments, the methods for preparing an implantable device comprise use of a low temperature process (e.g., from about 20° C. to about 100° C., more preferably from about 50° C. to about 90° C.) to form implants. In one embodiment, the method comprises a process that involves homogenously mixing the polymer and one or more bioactive agents in solvent, drying, and melt-extrusion-drawing the prepared solid into the implant shape. More specifically, the method comprises (a) dissolving one or more polymers in a suitable solvent solution to produce a complex fluid; (b) adding one or more bioactive agents to the complex fluid to produce a homogeneous solution of one or more bioactive agents and/or a solution with a dispersed phase of one or more bioactive agents; (c) drying the solution to a solid; heating the solid to a temperature below the melting point of the polymer (e.g., about 1° C. to about 5° C. below the melting point); (d) forming the implant device out of this semi solid; and (e) shaping the implant into the desired shape by drawing it into a elongated implant and mechanically sectioning it into a predetermined length. Optionally, the implant can be bent to add curvature. In some embodiments the complex fluid is not dried to a solid. In these embodiments, heating may not be required during the forming step because of the presence of the solvent in the complex fluid.

The steps of forming the implant device and shaping the implant into the desired shape can be accomplished by a variety of conventional methods for forming and shaping a device out of a solid. For example, the solid form may be processed by melt-extrusion-drawing (applying tensile force) to form the solid into the desired shape and thickness. The length can be modified by cutting the device with any conventional cutting tool. The distal and/or proximal ends of the implant can be shaped by cutting, sanding, and other methods for forming tapered, rounded, beveled and other desired end shapes.

In some embodiments, the implant is fabricated by: solubilizing poly(caprolactone) in chloroform at a temperature below boiling, overnight, under still or continuous stirring conditions; adding a bioactive agent to the solution in a ratio that preferably ranges from 1:99 to 70:30 (wt. bioactive agent: wt. polymer) depending on the prepared formulation; allowing the solvent to evaporate under still or stirring conditions after the solution becomes translucent or dispersed; transferring the solid-form of the loaded polymer to an extrusion device; heating the extrusion device to about 50° C. to about 90° C., depending on the molecular weight of the poly(caprolactone) ($M_n$=3,000 to 120,000), such that the polymer temperature approaches the melt temperature but does not exceed it; drawing the solid form to its desired geometry once the extrusion device reaches the desired sub melt temperature; shaping the implant to the desired implantation length after the temperature of the drawn implant falls.

When the implant comprises a core, the implant may be fabricated, for example, by applying a coating composition comprising one or more polymers and one or more bioactive agents over at least a portion of the outer surface of a core material. The coating composition can be applied to the outer surface of the core using any suitable method. For example, the coating composition may be applied by dipping, spraying, and other known methods for applying coating compositions to substrates. The suitability of the coating composition for use on a particular material can be evaluated by those skilled in the art.

In some embodiments, the coating composition is applied to the core utilizing a precision coating system where the coating composition is atomized ultrasonically (i.e., an ultrasonic coating system). Exemplary ultrasonic coating systems and methods are described in U.S. Published Application 2004/0062875 (Chappa et al.); and in U.S. application Ser. No. 11/102,465, filed Apr. 8, 2005, and entitled "Medical Devices and Methods for Producing Same". In some embodiments, a core (e.g., TiNi wire) to be coated is mounted in a pin vise, or similar device, that is capable of rotating the device about its longitudinal axis. The device is rotated and the ultrasonic spray head is passed back and forth relative to the rotating core.

Figure 15:
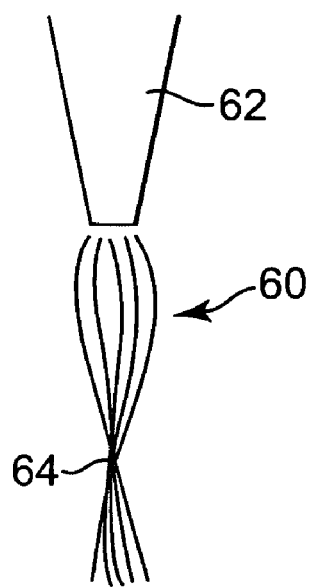
FIG. 15 is a representative schematic diagram of a spray stream that passes through a focal point.
Figure 16:
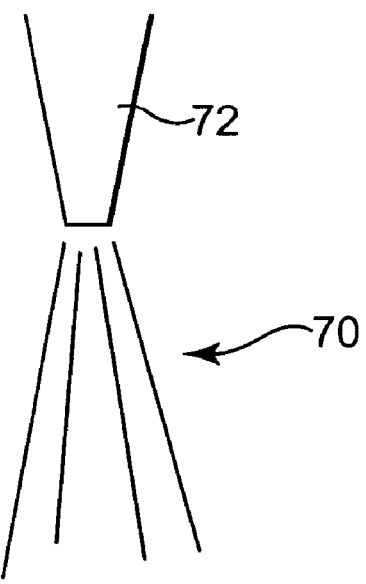
FIG. 16 is a representative schematic diagram of a spray stream that expands continuously as it moves away from the spray head.

Ultrasonic coating systems can produce a spray stream that narrows down as it moves away from the coating head. Referring to FIG. 15, the spray stream 60 narrows as it travels away from the coating head 62 before passing through a focal point 64 (or point of smallest spray stream diameter) before starting to expand. In an embodiment, the focal point has a cross-sectional diameter of about 0.5 mm to about 1.0 mm. In contrast, other types of spray systems frequently produce a spray stream that continuously expands in diameter as it leaves the spray head. Referring to FIG. 16, the spray stream 70 continues to get wider as it travels away from the coating head 72.

Ultrasonic coating systems can be used to coat a core with a large degree of accuracy, particularly where the core to be coated is positioned at or near the focal point of the spray stream. This is because the spray stream has a relatively small cross-sectional area at or near the focal point because the spray stream has a relatively small amount of spray droplets that are outside of the focal point. As the spray stream has a relatively small cross-sectional area, the position of the spray stream with respect to the core to be coated must be moved if a broader area of the core is to be covered with a coating. Either the core or the spray head may be moved to cover a broad area.

Figure 17:
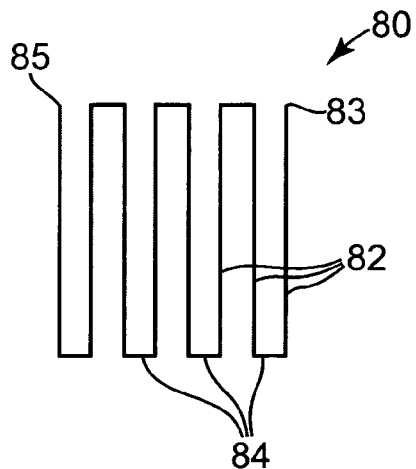
FIG. 17 is a representative schematic view of a grid-like coating pattern useful in coating implants of the invention.
Figure 18:
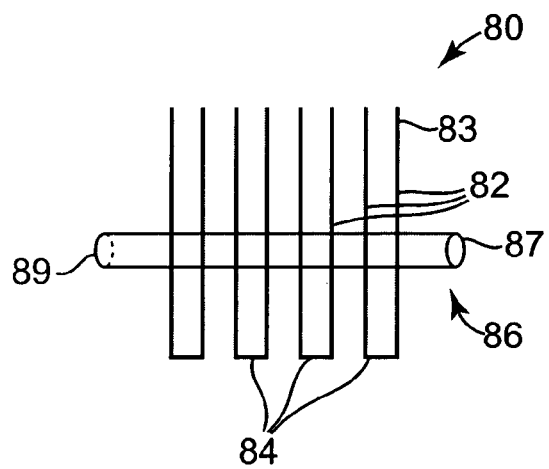
FIG. 18 is a representative schematic view of a grid-like coating pattern superimposed over a core material.

In an embodiment, the ultrasonic spray head is moved back and forth in a grid-like pattern over the rotating core. By way of example, an exemplary grid-like pattern 80 is shown in FIG. 17. The grid-like pattern starts at point 83 and ends at point 85. The grid like pattern has a series of transverse sweeps 82 and longitudinal movements 84. Depending upon the length of the longitudinal movements 84, any number of transverse sweeps can be used to cover the length of a given coating layer. In embodiments of the invention, the grid-like pattern 80 includes between 3 and 100 transverse sweeps 82. In embodiments of the invention, the grid-like pattern 80 includes between 3 and 100 longitudinal movements 84. Referring now to FIG. 18, grid-like pattern 80 is superimposed over an exemplary core material 86 having distal end 87 and proximal end 89 to illustrate how core material 86 would be coated with reference to the grid-like pattern 80.

The length of the longitudinal movements can be varied depending upon various factors including the cross-sectional diameter of the spray pattern as it meets the surface of the device to be coated. It has been found that when the longitudinal movements are greater than a desired amount, and when the grid-like pattern is followed from the same place on each pass, the surface of the coating may become bumpy. The specific limit on the size of the longitudinal movements will depend upon a number of factors including the diameter of the spray pattern and the relative spray density of various parts of the spray pattern.

In some embodiments, the ultrasonic coating head follows the grid-pattern multiple times (i.e., multiple passes) in order to deposit a coating layer onto a core. On each pass, an amount of the coating layer is deposited. Thus, the precise number of passes made by the ultrasonic coating head can be changed based on the total coating thickness desired. In some embodiments, the mass of the coating layer comprises between about 10 µg and about 1000 µg dry weight. In other embodiments, the mass of the coating layer comprises between about 50 µg to about 300 µg dry weight.

Figure 19:
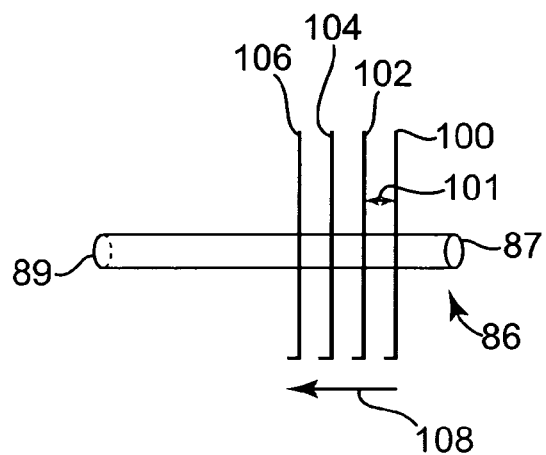
FIG. 19 is a representative schematic view of a series of first transverse sweeps superimposed over a core material.

In some embodiments, the same longitudinal starting position is used with respect to the core for each pass of the ultrasonic coating head. For example, for each pass, the ultrasonic coating head would start at the same longitudinal point and follow the same pattern. In other embodiments, the longitudinal starting position of the ultrasonic coating head may change with each additional pass. Referring to FIG. 19, the first transverse sweep of the first pass may start at point 100. Then, the first transverse sweep of the second pass may start at an offset position 102 that is offset at a distance 101 from starting point 100. Similarly, the first transverse sweep of the third pass and fourth pass begin at points 104 and 106, respectively. This technique of moving the starting position in the direction of arrow 108 can be used to extend the distance over which the coating builds up to its full thickness thereby controlling the slope of the transition segment of the coating layer. By way of example, the offset distance between successive passes could be 0.5 mm. This would generally result in a longer transition segment with a lower slope in comparison with a coating layer that was applied with an offset between successive passes of less than 0.5 mm, for example 0.2 mm. The slope of the transition segment may be desirably low (e.g., less than about 1.0) when the implant will undergo stresses (e.g., frictional stresses) that may result in delamination or failure of the coating. The slope of the transition segment may be desirably high (e.g., greater than about 1.0) where it is desired to maximize the amount of the coating layer on the implant. The proximal and distal transition segments of the coating layer may have slopes that are the same or different. For example, in some embodiments, the distal transition segment has a slope that is less than the proximal transition segment.

In some embodiments, the coating layer comprises at least two layers, wherein each layer comprises the same composition, or comprises different compositions. In one such embodiment, a first layer having either bioactive agent alone, or bioactive agent together with one or more of the polymers (first polymer and/or second polymer) is applied, after which one or more additional layers are applied, each with or without bioactive agent. These different layers, in turn, can cooperate in the resultant composite coating to provide an overall release profile having certain desired characteristics, and is particularly preferred for use with bioactive agents having high molecular weight. According to the invention, the composition of individual layers of the coating can include any one or more of the following: one or more bioactive agents, a first polymer, and/or a second polymer, as desired.

Preferably, the coating composition is applied to the core of the implant in one or more applications. The method of applying the coating composition to the body member is typically governed by such factors as the geometry of the device and other process considerations. The coated composition can be subsequently dried by evaporation of the solvent. The drying process can be performed at any suitable temperature, (for example, room temperature or elevated temperature), and optionally with the assistance of vacuum.

In some preferred embodiments, the coating composition is applied to the core under conditions of controlled relative humidity. As used herein, "relative humidity" is the ratio of the water vapor pressure (or water vapor content) to the saturation vapor pressure (or the maximum vapor content) at a given temperature of the air. The saturation vapor pressure in the air varies with air temperature: the higher the temperature, the more water vapor it can hold. When saturated, the relative humidity in the air is 100% relative humidity. According to some embodiments of the invention, the coating composition can be applied to the core under conditions of increased or decreased relative humidity as compared to ambient humidity.

According to the invention, humidity can be controlled in any suitable manner, including at the time of preparing and/or applying the coating composition to the body member. For example, when humidity is controlled at the time of preparing the coating composition, the water content of the coating composition can be adjusted, before and/or after the coating composition is applied to the body member. When humidity is controlled at the time of applying the coating composition, the coating composition can be applied to the body member in a confined chamber or area adapted to provide a relative humidity that differs from ambient humidity. Generally, it has been found that applying coating compositions under conditions of increased humidity will typically accelerate release of the bioactive agent, while applying coating compositions under conditions of decreasing humidity levels will tend to decelerate release of the bioactive agent. As contemplated in the invention, even ambient humidity can be considered "controlled" humidity if it has been correlated with and determined to provide a corresponding controlled release of the bioactive agent.

Moreover, and particularly when coating a plurality of coating compositions onto the body member of the controlled delivery device to provide the final coated composition, humidity can be controlled in different ways (for example, using a controlled environment as compared to adjusting the water content of the coating composition) and/or at different levels to provide a desired release profile for the resulting coated composition. As described previously, a coated composition can be provided using a plurality of individual steps or layers of coating composition, including, for instance, an initial layer having only bioactive agent (or bioactive agent with one or both polymers), over which is coated one or more additional layers containing suitable combinations of bioactive agent, first polymer, and/or second polymer, the combined result of which is to provide a coated composition of the invention.

Thus, in preferred embodiments, the invention provides the ability to reproducibly control the release of a bioactive agent from a controlled delivery device.

In some embodiments, a plurality of coating compositions and corresponding coating steps can be employed, each with its own controlled humidity (when desired), in order to provide a desired combination of layers, each with its corresponding release profile. Those skilled in the art will appreciate the manner in which the combined effect of these various layers can be used and optimized to achieve various effects in vivo.

The implant can be of any geometric shape and size that can be readily inserted into the eye. Further, once inserted, the implant should not be sized and/or shaped so as to interfere with the functions of the eye and should not cause unnecessary discomfort or damage to the eye. In some embodiments, the implant is rod-like or filament-like in shape. However, the geometry of the device is not limited to filament or rod shapes but, rather, it may also be provided in any other shape suitable for insertion into the eye (e.g., curved or C-shaped devices, coils, thin films, ribbons, foldable discs, pellets, etc.). In some embodiments, the implant is designed so as to facilitate insertion within the eye. For example, the distal end of the implant may be beveled, tapered, or sharpened so as to facilitate eye entry and/or penetration. Alternatively, the distal end may be blunt or rounded and the device may be inserted through an incision in the eye. While providing an implant with a sharpened distal end may facilitate penetration and entry into the eye, it can potentially make it more challenging for the user to position the implant and may contribute to the implant crossing multiple retinal tissue layers rather than conforming itself into the subretinal space at its final resting position (see, for example, FIGS. 2-3). However, these potential results can be overcome by the use of implantation techniques wherein these factors are taken into account, or by providing an implant with a blunt or rounded distal end. The implant is designed to provide sustained delivery of bioactive agent(s) without major trauma or the need for fluid dissection of the retina.

In some embodiments, the outer diameter of the implant is no greater than about 1000 μm to minimize the incidence of retinal detachments and hemorrhaging. In other embodiments, the outer diameter of the implant is 900 μm or less, in other embodiments 800 μm or less, in other embodiments 700 μm or less, in other embodiments 600 μm or less, in other embodiments 500 μm or less, in other embodiments 400 μm or less, in other embodiments 300 μm or less, in other embodiments 200 μm or less. In some embodiments the diameter of the implant ranges from about 200 μm to about 500 μm.

In some embodiments, the length of the implant is no greater than about 5 mm, in other embodiments no greater than 4.5 mm, in other embodiments no greater than 4.0 mm, in other embodiments no greater than 3.5 mm. In a specific embodiment the implant is no greater than about 3 mm in length as such lengths have been found to provide the additional benefit of coming to a final resting point within the eye that does not cross multiple tissue layers. However, it is possible to provide implants longer than 3 mm that can be inserted with special care so as to minimize the incidence of multiple tissue layer crossing. The flexibility of the implant can allow it to conform to its final implanted resting position. In yet further embodiments, the length of the implant is 2.9 mm or less, in other embodiments 2.8 mm or less, in other embodiments 2.7 mm or less, in other embodiments 2.6 mm or less, in other embodiments 2.5 mm or less, in other embodiments 2.4 mm or less, in other embodiments 2.3 mm or less, in other embodiments 2.2 mm or less, in other embodiments 2.1 mm or less, and in other embodiments 2.0 mm or less. In some embodiments, the length of the implant ranges from about 2.00 mm to about 3.00 mm.

As the implant becomes smaller in diameter, the insertion and handling of the device becomes more difficult and the amount of bioactive agent(s) that can be encapsulated in the implant is limited. Such factors are taken into account in determining the size of the implant. In some embodiments, the implant is sufficiently rigid to be grasped by a microsurgical instrument that can direct it into the subretinal space and, thus, the implant is designed accordingly. Similarly, as the implant becomes smaller in length, the insertion and handling of the device becomes more difficult and the amount of bioactive agent(s) that can be encapsulated in the implant is reduced. Thus, these factors are taken into account in determining the size of the implant. In one embodiment, the cross-sectional surface area of the device is preferably up to 196250 $\mu m^2$.

In some embodiments, the implants are inserted directly into the eye "as is". In other embodiments, implant insertion devices (for example, a tube-like device in which the implant is loaded and inserted into the eye) may be used to facilitate insertion of the implant into the subretinal space. Such insertion devices can eliminate the need to use micro-forceps and similar devices to load and position the implant within the eye.

As used herein "bioactive agent" refers to an agent that affects physiology of biological tissue. Bioactive agents useful according to the invention include virtually any substance that possesses desirable therapeutic characteristics for application to the implant site. For the purpose of the description herein, reference will be made to "bioactive agent", but it is understood that the use of the singular term does not limit the application of bioactive agents contemplated, and any number of bioactive agents can be provided using the teaching herein.

The bioactive agents can include, but are not limited to, drugs, medicaments, antibiotics, antibacterials, antiproliferatives, neuroprotectives, anti-inflammatories (steroidal and non-steroidal), growth factors, neurotropic factors, antiangiogenics, thrombolytics or genes.

Exemplary bioactive agents include, but are not limited to, thrombin inhibitors; antithrombogenic agents; thrombolytic agents; fibrinolytic agents; vasospasm inhibitors; calcium channel blockers; vasodilators; antihypertensive agents; antimicrobial agents, such as antibiotics (such as tetracycline, chlortetracycline, bacitracin, neomycin, polymyxin, gramicidin, cephalexin, oxytetracycline, chloramphenicol, rifampicin, ciprofloxacin, tobramycin, gentamycin, geldanamycin, erythromycin, penicillin, sulfonamides, sulfadiazine, sulfacetamide, sulfamethizole, sulfisoxazole, nitrofurazone, sodium propionate), antifungals (such as amphotericin B and miconazole), and antivirals (such as idoxuridine trifluorothymidine, acyclovir, gancyclovir, interferon); inhibitors of surface glycoprotein receptors; antiplatelet agents; antimitotics; microtubule inhibitors; anti-secretory agents; active inhibitors; remodeling inhibitors; antisense nucleotides; anti-metabolites; antiproliferatives (including antiangiogenesis agents); anticancer chemotherapeutic agents; anti-inflammatories (such as hydrocortisone, hydrocortisone acetate, dexamethasone 21-phosphate, fluocinolone, medrysone, methylprednisolone, prednisolone 21-phosphate, prednisolone acetate, fluorometholone, betamethasone, triamcinolone, triamcinolone acetonide); non-steroidal anti-inflammatories (such as salicylate, indomethacin, ibuprofen, diclofenac, flurbiprofen, piroxicam); antiallergenics (such as sodium chromoglycate, antazoline, methapyriline, chlorpheniramine, cetrizine, pyrilamine, prophenpyridamine); anti-proliferative agents (such as 1,3-cis retinoic acid); decongestants (such as phenylephrine, naphazoline, tetrahydrazoline); miotics and anti-cholinesterase (such as pilocarpine, salicylate, carbachol, acetylcholine chloride, physostigmine, eserine, diisopropyl fluorophosphate, phospholine iodine, demecarium bromide); antineoplastics (such as carmustine, cisplatin, fluorouracil); immunological drugs (such as vaccines and immune stimulants); hormonal agents (such as estrogens, estradiol, progestational, progesterone, insulin, calcitonin, parathyroid hormone, peptide and vasopressin hypothalamus releasing factor); immunosuppressive agents, growth hormone antagonists, growth factors (such as epidermal growth factor, fibroblast growth factor, platelet derived growth factor, transforming growth factor beta, somatotropin, fibronectin); inhibitors of angiogenesis (such as angiostatin, anecortave acetate, thrombospondin, anti-VEGF antibody); dopamine agonists; radiotherapeutic agents; peptides; proteins; enzymes; extracellular matrix components; ACE inhibitors; free radical scavengers; chelators; antioxidants; anti-polymerases; photodynamic therapy agents; gene therapy agents; and other therapeutic agents such as prostaglandins, antiprostaglandins, prostaglandin precursors, and the like.

Antiproliferatives include any of a number of compounds, agents, therapeutic mediums or drugs known to those skilled in the art that inhibit the proliferation of cells. Such compounds, agents, therapeutic mediums or drugs include, but are not limited to, 5-fluorouracil, taxol, rapamycin, mitomycin C and cisplatin.

Neuroprotectives include any of a number of compounds, agents, therapeutic mediums or drugs known to those skilled in the art that guard or protect against neurotoxicity; the quality of exerting a destructive or poisonous effect upon nerve tissue. Such compounds, agents, therapeutic mediums or drugs include, but are not limited to, lubezole.

Anti-inflammatories include any of a number of compounds, agents, therapeutic mediums or drugs known to those skilled in the art, either steroidal or non-steroidal, and generally characterized as having the property of counteracting or suppressing the inflammatory process. Non-steroidal inflammatory drugs or compounds comprise a class of drugs which shares the property of being analgesic, antipyretic and anti-inflammatory by way of interfering with the synthesis of prostaglandins. Such non-steroidal anti-inflammatories include, but are not limited to, indomethacin, ibuprofen, naproxen, piroxicam and nabumetone.

Such anti-inflammatory steroids contemplated for use in the methodology of the invention, include those described in U.S. Pat. No. 5,770,589. In an exemplary embodiment, an anti-inflammatory steroid contemplated for use in the methodology of the invention is triamcinolone acetonide (generic name). Corticosteroids contemplated for use in the methodology of the invention include, for example, triamcinolone, dexamethasone, fluocinolone, cortisone, prednisolone, flumetholone, and derivatives thereof (See also, U.S. Pat. No. 5,770,589).

As is known to those skilled in the art, growth factors is a collective term originally used to refer to substances that promote cell growth and is now loosely used to describe molecules that function as growth stimulators (mitogens) but also as growth inhibitors (sometimes referred to as negative growth factors), factors that stimulate cell migration, or as chemotactic agents or inhibit cell migration or invasion of tumor cells, factors that modulate differentiated functions of cells, factors involved in apoptosis, factors involved in angiogenesis, or factors that promote survival of cells without influencing growth and differentiation. In the invention, such growth factors include, but are not limited to, pigment epithelium derived factor and basic fibroblast growth factor.

As is known to those skilled in the art, neurotropic factors is a general term used to describe growth factors and cytokines that can enhance neuronal survival and axonal growth and that regulate synaptic development and plasticity in the nervous system. In the invention, such growth factors include, but are not limited to, ciliary neurotrophic factors and brain-derived neurotrophic factors.

Antiangiogenics include any of a number of compounds, agents, therapeutic mediums or drugs known to those skilled in the art that inhibit the growth and production of blood vessels, including capillaries. Such compounds, agents, therapeutic mediums or drugs include, but are not limited to, anecortave acetate and anti VEGF antibody.

Thrombolytics, as is known to those skilled in the art include any of a number of compounds, agents, therapeutic mediums or drugs that dissolve blot clots, or dissolve or split up a thrombus. Such thrombolytics include, but are not limited to, streptokinase, tissue plasminogen activator or TPA and urokinase.

The bioactive agent composition within the implant can additionally be selected so as to modify the physical properties of the polymer used in forming the matrix so as to provide additional flexibility or rigidity as desired. Such selection can be readily accomplished by one of skill in the art given the polymer being used and the desired modification. For example, with some bioactive agents a higher bioactive agent loading yields a softer material.

In some embodiments, the implant has a bioactive agent elution rate of at least 0.0001 μg per day, in other embodiments at least 0.001 μg per day, in other embodiments at least 0.01 μg per day, in other embodiments at least 0.1 μg per day, in other embodiments at least 1 μg per day, in other embodiments at least 10 μg per day, in other embodiments at least 100 μg per day, and in other embodiments at least 1000 μg per day. The elution rate can vary and can be customized as desired for each type of eye condition treated, the selected bioactive agent(s), and the severity of the condition being treated. In general, it is desired to maximize the total bioactive agent(s) loading while maintaining mechanical integrity of the implant.

Implants of the invention provide significant advantages because they are designed for insertion, implantation and bioactive agent delivery directly at the desired treatment site (i.e., the portion of the eye being treated). In some embodiments, the implants are designed for the treatment of disorders or diseases of the choroid and the retina. As such, the implants are inserted and implanted directly in the choroid, the retina or subretinal space, so as to deliver the bioactive agent precisely to the portion of the tissue being treated. Such localized delivery is efficient and delivers the bioactive agent substantially only to the portion of the eye being treated and does not deliver any significant amount of bioactive agent to healthy tissues. As used herein, the terminology delivered substantially only to the portion of the eye being treated is understood to mean that at least 5%, more preferably at least 10%, more preferably at least 20%, more preferably at least 30%, more preferably at least 40%, more preferably at least 50%, more preferably at least 60%, more preferably at least 70%, more preferably fit least 75%, more preferably at least 80% more preferably at least 85%, more preferably at least 90%, more preferably at least 91%, more preferably at least 92%, more preferably at least 93%, more preferably at least 94%, more preferably at least 95%, more preferably at least 96%, more preferably at least 97%, more preferably at least 98%, more preferably at least 99%, more preferably all of the bioactive agent delivered by the implant is delivered to the portion of the eye being treated. As used herein, the terminology "does not deliver any significant amount of bioactive agent to healthy tissues" is understood to mean that less than 95%, more preferably less than 90%, more preferably less than 80%, more preferably less than 70%, more preferably less than 60%, more preferably less than 50%, more preferably less than 40%, more preferably less than 30%, more preferably less than 20%, more preferably less than 15%, more preferably less than 10%, more preferably less than 5%, more preferably less than 4%, more preferably less than 3%, more preferably less than 2%, more preferably less than 1% of the total bioactive agent delivered by the implant is delivered to healthy tissue.

This is in contrast to, systemic, topical, and whole organ delivery mechanisms that have previously been used to treat diseases and disorders of the eye, such mechanisms require the administration of significantly larger dosages of bioactive agents systemically, topically, orally or organ-wide so as to deliver a therapeutically effective amount of bioactive agent to the treatment site. For example, in order to administer a therapeutically effective dose of bioactive agent to treat a retinal disorder, approximately 1000 to 1,000,000 times the therapeutically effective dose may need to be administered systemically or orally. Not only does this result in the unnecessary waste of bioactive agent, but it also can cause undesirable toxicity and/or side effects from the delivery of such large amounts of bioactive agent. In some cases the systemic, oral and whole organ toxicity is so severe that a therapeutic dose may not be achievable by these conventional methods of administration. Further such delivery systems deliver bioactive agent to tissue and portions of the body that do not require the administration of such bioactive agent. In general, for example, such delivery systems deliver the bioactive agent to diseased and non-diseased portions of the eye. Likewise, whole organ delivery systems are also inefficient and require the delivery of substantially larger dosages of bioactive agents so as to provide a therapeutically effective amount of agent to the treatment site. As used herein, "local organ delivery system" is understood to mean a delivery system that delivers a bioactive agent generally to the organ being treated. Thus, for example, a local, whole visual/eye organ delivery system used to treat a retinal disease would deliver a bioactive agent to the diseased organ (the eye) rather than the diseased portion of the organ. The drawback with such systems is that the whole visual/eye organ receives a therapeutic level of drug even though only the diseased portion of the organ (e.g. the retina) actually requires treatment. Nonetheless, such local organ delivery systems deliver the bioactive agent to the entire eye, including the diseased tissues of the retina and healthy tissues of the eye. Further, such systems deliver the bioactive agent to a portion of the eye some distance away from the desired treatment site. As a result, the amount of bioactive agent that must be administered to the organ (the entire eye) may be in excess of the therapeutically effective dosage that would be required to treat the disorder or disease if the bioactive agent was delivered directly and only to the diseased eye tissues. For example, in order to administer a therapeutically effective dose to treat a retinal disorder, approximately 100 to 1000 times the therapeutically effective dose must be administered using whole organ delivery systems. The administration of bioactive agent to portions of an organ that do not require such administration may cause undesirable toxicity or side effects. For example, the delivery of a bioactive agent to an eye having a retinal disorder, but that is otherwise healthy, can potentially cause cataracts, raised intraocular pressure, and blurred vision from precipitated drug in the vitreous. While treatment of the retina and choroid of the eye has been discussed in particular, it is to be understood that the implants may similarly be used for the treatment of other ocular site specific disorders.

Because the present implants are more efficient than whole organ delivery systems they have a more discrete geometry than whole organ delivery systems. In particular, because whole organ delivery systems are required to hold and deliver a larger amount of bioactive agent to achieve the same therapeutic drug level at the disease site and, they are designed so as to maximize the amount of bioactive agent that can be held and delivered. Thus, for example, larger implants and/or implants with complex geometries (e.g. coiled or curved profiles) are required to provide a greater surface area and/or a larger interior reservoir for holding bioactive agent. The present implants need not hold such large quantities of bioactive agent and thus, need not possess larger and/or more complex geometries, although they may if desired.

The invention also features methods for the treatment and prevention of disorders and or diseases of the eye, in particular retinal/choroidal disorders or diseases, by administering to a desired treatment site, particularly the choroid and the retina, one or more bioactive agents. In particular, the methods provide administering one or more bioactive agents to a treatment site by implanting the bioactive agents within the eye. In one embodiment, an implant of the invention is inserted within the eye to provide sustained delivery of the bioactive agent to the desired treatment site. Such methods provide localized, sustained delivery of the bioactive agent subretinally at the treatment site without major trauma or the need for fluid dissection of the retina.

In a preferred method, the implant is located in one or more tissue layers above the choroid below the nerve fiber layer. Further, if desired, two or more implants may be simultaneously implanted, potentially encircling the disease site. Further, it is desired that the implant acts both as a sustained release drug delivery system and as a body that is capable of self-piercing and/or penetrating the eye structure to achieve implantation within the eye. However, it is also possible to provide an incision in the eye through which the implant is inserted.

One method for inserting the implant involves performing a standard pars plana vitrectomy, and inserting the implant into the subretinal space through the pars plana vitrectomy. In particular, the subjects are first anesthetized, for example, with an intramuscular injection of ketamine hydrochloride and xylazine hydrochloride. Next the pupils are dilated with phenylephrine and tropicamide. A peritomy is then made at the superotemporal and superonasal quadrants. An infusion pipe line may be inserted through the superonasal sclerotomy and a vitreous cutter inserted through the superotemporal sclerotomy. The vitreous cutter and infusion pipe may then be used to perform a 2-port core vitrectomy. The illumination provided by an operating microscope is sufficient for the operation. Using intraocular microscopic forceps, the implant is inserted in the subretinal space through a small self-starting retinotomy. The implant may have a bevel shaped tip, thereby facilitating insertion into the subretinal space. The implant is left in position and the forceps withdrawn from the eye. No laser retinopexy need be applied to seal the retinal break. The infusion line is removed and the sclerotomies and conjunctival openings closed.

It has further been found that the bioactive agent concentration is a function of the distance between the implant and tissue layers and, thus, the placement of the implant can be customized to provide particular concentrations of bioactive agents with a specific dose/distance relationship to the circumferential or spherical radius of the eluting source. It has been further found that an array of implants can be used in combination to further customize the dose. For example, where the circumferential or spherical radius dose/distance relationship of two or more implants overlap, one or more zones of different bioactive agent concentrations could be achieved.

Most, if not all, ophthalmic diseases and disorders are associated with one or more of three types of indications: (1) angiogenesis, (2) inflammation, and (3) degeneration. Based on the indications of a particular disorder, one of ordinary skill in the art can administer any suitable bioactive agent from the three groups at a therapeutic dosage. The following describes some ophthalmic diseases and disorders and a form of treatment therefore. It should be recognized, however, that the following is by way of illustration and is not intended to limit the methodologies of the invention to a particular technique or bioactive agent for treatment of an eye disease or disorder.

Diabetic retinopathy, for example, is characterized by angiogenesis. This invention contemplates treating diabetic retinopathy by delivering one or more anti-angiogenic factors into the subretinal space. It also is desirable to co-deliver one or more neurotrophic factors also to the subretinal space.

Uveitis involves inflammation. The invention contemplates treating uveitis by instilling or disposing one or more anti-inflammatory factors in the subretinal space.

Retinitis pigmentosa, by comparison, is characterized by retinal degeneration. The invention contemplates treating retinitis pigmentosa by instilling or disposing one or more neurotrophic factors in the subretinal space.

Age-related macular degeneration involves both angiogenesis and retinal degeneration and includes, but is not limited to, dry age-related macular degeneration, exudative age-related macular degeneration, and myopic degeneration. The invention contemplates treating this disorder by instilling or disposing in the subretinal space one or more neurotrophic factors and/or one or more anti-angiogenic factors. More particularly, the methodology contemplates instilling or disposing a corticosteriod in the subretinal space.

Glaucoma is characterized by increased ocular pressure and loss of retinal ganglion cells. Treatments for glaucoma contemplated in the invention include delivery of one or more neuroprotective agents that protect cells from excitotoxic damage. Such agents include N-methyl-D-aspartate (NMDA) antagonists, cytokines, and neurotrophic factors.

The invention will be further illustrated with reference to the following examples which are intended to aid in the understanding of the present invention, but which are not to be construed as a limitation thereof.

EXAMPLES

Example 1

Materials Used

Poly(caprolactone) (Average Mw 80,000, $[-O(CH_2)_5CO-]_n$, Melt index 125° C./0.3 MPa, Sigma Aldrich Biochemicals, St. Louis, Mo.)
Triamcinolone acetonide (TA) (Purity 99%, $M_n$ 434.5, $C_{24}H_{31}FO_6$, Sigma Aldrich Biochemicals, St. Louis, Mo.)
Prednisolone Purity 99%, $C_{21}H_{28}O_5$, $M_n$ 360.5, Sigma Aldrich Biochemicals, St. Louis, Mo.)
Chloroform (purity 99.8%, $CHCl_3$, A.C.S. spectroscopic grade, Sigma Aldrich Chemicals)
Ether (purity 99%, $M_n$ 74.12, $(C_5H_5)_2O$ A.C.S. reagent, Sigma Aldrich Chemicals)
Balanced salt solution (Sterile, preservative free, Akorn, Inc., Somerset, N.J.)
Bovine serum albumin (Molecular biology grade, Sigma Aldrich Biochemicals, St. Louis, Mo.)
Abbreviations:
PCL: poly(caprolactone) biodegradable implant
TA: triamcinolone
PCL/TA: biodegradable triamcinolone loaded poly(caprolactone) implants
Implant Preparation:

The implants used in the example were prepared as follows. PCL was solubilized in chloroform at 35° C. overnight under continuous stirring conditions. Triamcinolone acetonide (TA) was then added to the solution in a polymer/drug weight ratio ($w_p/w_D$) of 70:30, 60:40 or 50:50. Once the solution became homogeneous, it was poured onto an evaporating tray and left in a fume hood for 72 hours to solidify. The white solid-form sheath of the TA loaded PCL was rolled into a tight column and packed into a 10 mL syringe. The syringe was heated to 80° C. in a water bath to ensure even heat distribution and to prevent high localized temperatures that could damage the drug or polymer. Although the polymer was not fully in the melt state, the temperature was sufficiently high to initiate the transition of this semi-crystalline closed packed macromolecular polymer to a sufficiently viscous state to be extruded. Additionally, it was noted that drug crystals within the polymer acted as a "flow enhancing" plasticizer when comparing the process to a PCL only implant extrusion.

Once the syringe reached 80° C. it was rapidly removed from the water bath and 1 cm of material was extruded from it. The extruded material was subsequently drawn to a filament by imparting a tensile force. For the 70:30, 60:40 or 50:50 $w_p/w_D$ formulations, ~150 μm implant diameters were achieved by a drawing length of approximately 20, 15 and 10 cm, respectively, while ~300 μm implant diameters were achieved by a drawing length of approximately 15, 10 and 5 cm, respectively. The formulation with the highest drug load (50:50 $w_p/w_D$) broke more frequently during the drawing process. The drawn implant cooled rapidly and could be subsequently cut under a microscope to the desired implantation length.

Implants without drug were also prepared by directly inserting the PCL pellets into the syringe, heating them to 80° C. and then extruding and drawing in a similar manner to that previously described.

Six pigmented rabbits underwent fluorescein angiography, fundus photography, and optical coherence tomography (Zeiss Model 3000, Germany) at baseline and 4 weeks after implantation. The rabbits were subdivided into the following groups:

Group 1: 2 rabbits with PCL only implants (PCL, Rabbits 1 and 2);
Group 2: 4 rabbits with PCL/TA 60:40 ($w_p/w_D$) implants (Rabbits 3-6).

Both groups underwent standard pars plana vitrectomy, and insertion of the drug delivery device into the subretinal space. Briefly, animals were anesthetized with an intramuscular injection of 0.3 mL of ketamine hydrochloride (100 mg/mL; Fort Dodge Lab., Iowa) and 0.1 mL of xylazine hydrochloride (100 mg/mL; Miles Inc, USA) per kilogram of body weight. Pupils were dilated with 1 drop each of 2.5% phenylephrine and 1% tropicamide. A 3-mm peritomy was made at the superotemporal and superonasal quadrant of the right eye. Sclerotomies were created with a 20-gauge microvitreoretinal blade 1 to 2 mm posterior to the limbus in the superotemporal and superonasal quadrants. An infusion line was inserted and sutured through the superonasal sclerotomy and a vitreous cutter (Bausch & Lomb, USA) was inserted through the superotemporal sclerotomy. The vitreous cutter and infusion line were used to perform a 2-port core vitrectomy. The illumination provided by the operating microscope (Zeiss, Germany) was sufficient for the operation.

Using intraocular microscopic forceps (Bausch & Lomb, USA), the implants were inserted in the subretinal space through a small self-sealing retinotomy. The beveled tip of the implant allowed easy insertion through the retina. The implant was left in position and the forceps was withdrawn from the eye. No laser retinopexy was applied to seal the retinal breaks. The infusion line was removed and the sclerotomies and conjunctival openings were closed using Vycril 7-0 (Ethicon, USA). During week 4, all rabbits underwent fundus examination and were then sacrificed under anesthesia using an intracardiac injection of pentobarbital sodium (Anpro Pharmaceuticals, Oyster Bay, N.Y.).

Elution, Drug Extraction and Histology:
In Vitro Elution

For in vitro drug elution characterization, drug-loaded PCL implants were prepared according to Table 1.

TABLE 1

In vitro sample parameters

| Sample | Formulation (PCL/TA) | Diameter (μm) | Length (mm) |
|---|---|---|---|
| 1 | 70:30 | 210 | 30 |
| 2 | 70:30 | 210 | 30 |
| 3 | 70:30 | 250 | 30 |
| 4 | 70:30 | 250 | 30 |
| 5 | 70:30 | 360 | 30 |
| 6 | 60:40 | 150 | 30 |
| 7 | 60:40 | 150 | 30 |
| 8 | 60:40 | 320 | 30 |
| 9 | 60:40 | 320 | 30 |
| 10 | 50:50 | 150 | 30 |
| 11 | 50:50 | 150 | 30 |
| 12 | 50:50 | 320 | 30 |
| 13 | 50:50 | 320 | 30 |

Each implant was placed in a 15 mL capped tube containing 10 mL of a 1% bovine serum albumin (BSA)/balance salt solution (BSS). Tubes were incubated at 37° C. in a shaking water bath (100 rpm). At each time increment of 2, 4, 8, 24, 72, 168, 336, 504 and 672 hours, the implants were removed from the BSS/BSA solution and placed into a new 10 ml BSS/BSA solution.

After the final time period, the implants were removed from the BSS/BSA solution and placed in tubes containing 2 mL of ether for complete extraction of the remaining TA. Ether (2 mL) and a 50 µL of internal standard (prednisolone 2 mg/ml) were added to the remaining BSS/BSA solutions. Each solution was vortexed for 2 min and then centrifuged for 3 min at 10,000 rpm to separate the ether and BSS/BSA phases. The top layer ether phase was removed using a glass syringe and added to a 2 mL capped microtube for solvent evaporation in fume hood. Following complete evaporation, 1 mL of 60% methanol was added to the microtube and vortexed. The solution was then transferred to a 1 mL glass shell high performance liquid chromatography (HPLC) vial for analysis.

In Vivo Elution

Two rabbits (PCL/TA 60:40 implants) were used for analysis of in vivo drug elution. Rabbits were anesthetized prior to the collection of aqueous (~0.3 mL) and blood into lithium heparin tube (2 mL). Rabbits were then euthanized and the eyes enucleated. The implanted device and surrounding tissues (sclera, choroid, retina, lens, and vitreous) were dissected and separated into 2 mL micro tubes. Individual tissue was weighed and then homogenized in 0.5 mL BSS by sonication (1-2 pulse/sec at 50% power). Once completed, samples were enriched with 50 µL internal standard (prednisolone 2 mg/ml) and vortexed. TA was extracted from the tissue sample by adding ether (0.5 mL), vortexing and centrifuging at 10,000 rpm for 10 min. The top ether layer was removed and placed in a new 2 mL microtube for evaporation and substitution of the solvent for methanol as previously described in the in vivo study.

A Millennium high performance liquid chromatograph (Waters Corp., USA) equipped with a 515 pump, 2996 photodiode array detector and 717-plus autosampler injector was used in this study to process the in vitro and in vivo samples. The Millennium software provided with the high performance liquid chromatograph (HPLC) was used for integration of chromatographic peaks. The solvents were linked to an in-line degasser. The samples were injected into reverse phase HPLC system consisting of stationary phase of Nova-Pak C 18 column (3.9×150 mm) and Nova-Pack guard column (Waters Corp., USA); and an isocratic mobile phase of 60% methanol. The peaks of TA and prednisolone were eluted at a flow rate of 1 mL/min with detection at 245 nm. Parallel 50 µL of prednisolone was chromatogramed under the same HPLC condition to determine the extraction efficiency of TA. Further, the co-chromatography technique was adopted to validate the identification of both compounds. The calculation of TA concentration was based on the area peaks and percentage recovery of prednisolone. The HPLC condition separated the peaks of triamcinolone and prednisolone with good resolution. The retention time of prednisolone was 3.46 minutes while that of triamcinolone was 5.2 minutes.

Histology

The eyes of the four remaining rabbits (2 rabbits with PCL only implants; 2 rabbits with PCL/TA 60:40 implants) were enucleated and fixed in 4% paraformaldehyde for 24 hours and then Bouin's fixative for a further 24 hours. The specimens were then embedded in paraffin, sectioned, and hematoxylin and eosin (H & E) stained under standard histology laboratory conditions.

Figure 1:
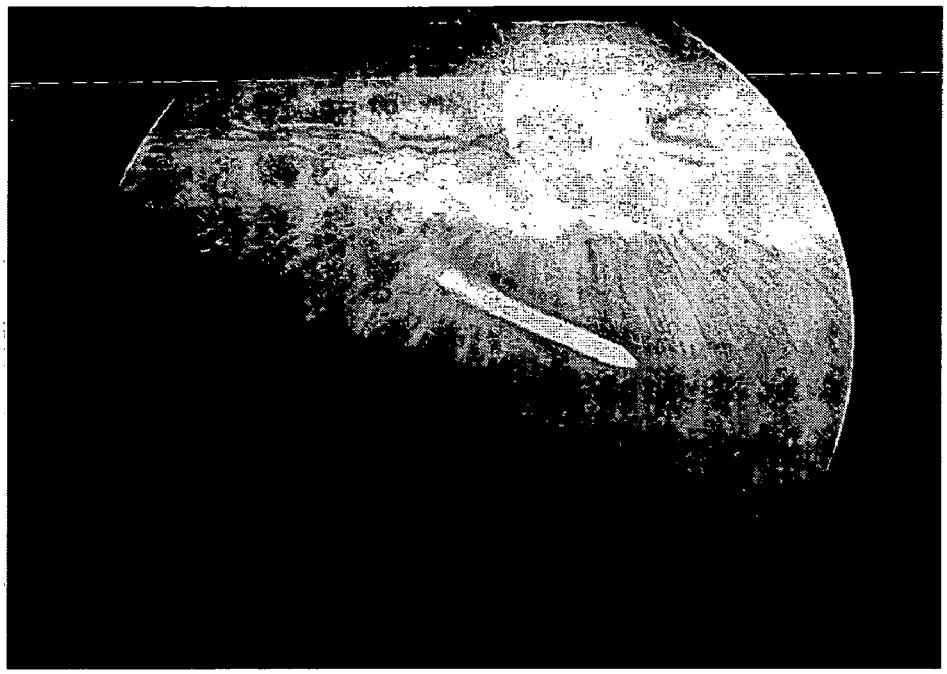
FIG. 1 shows a representative fundus photography of an implanted poly(caprolactone)/triamcinolone acetonide (PCL/TA) implant in accordance with one embodiment of the invention, at 4 weeks after implant.
Figure 2:
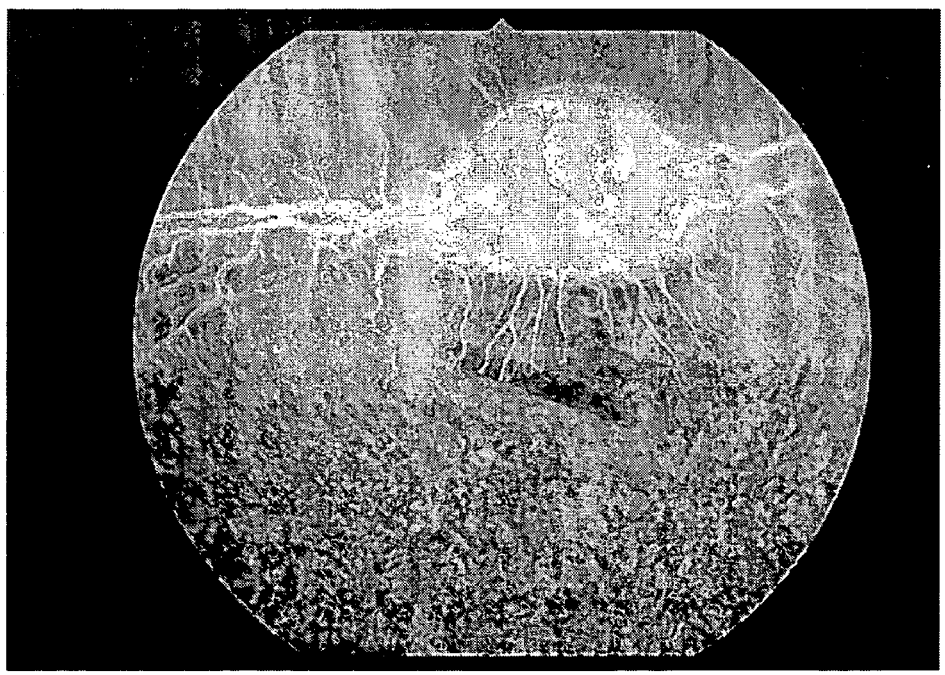
FIG. 2 shows a representative fluorescein angiography of an implanted PCL/TA implant in accordance with one embodiment of the invention, at 4 weeks after implant.

Results:

Clinical examination using slit-lamp and indirect ophthalmoscopy at 1, 2, 3 and 4 weeks showed that there was no detectable accumulation of subretinal fluid, exudates, hemorrhage or fibrosis surrounding the device at any of the follow up points. Fundus photography showed that the implant maintained its position without signs of inflammation or migration, as shown in FIG. 1 for a representative rabbit. Fluorescein angiography demonstrated the absence of vascular leakage, pooling, retinal pigmented epithelium (RPE) abnormalities, or fibrosis at any of the follow-up points for a representative rabbit, as shown in FIGS. 1-2. Optical coherence tomography revealed the successful placement of the implant in the subretinal space of all the rabbit eyes, as shown in FIG. 3.

Figure 3:
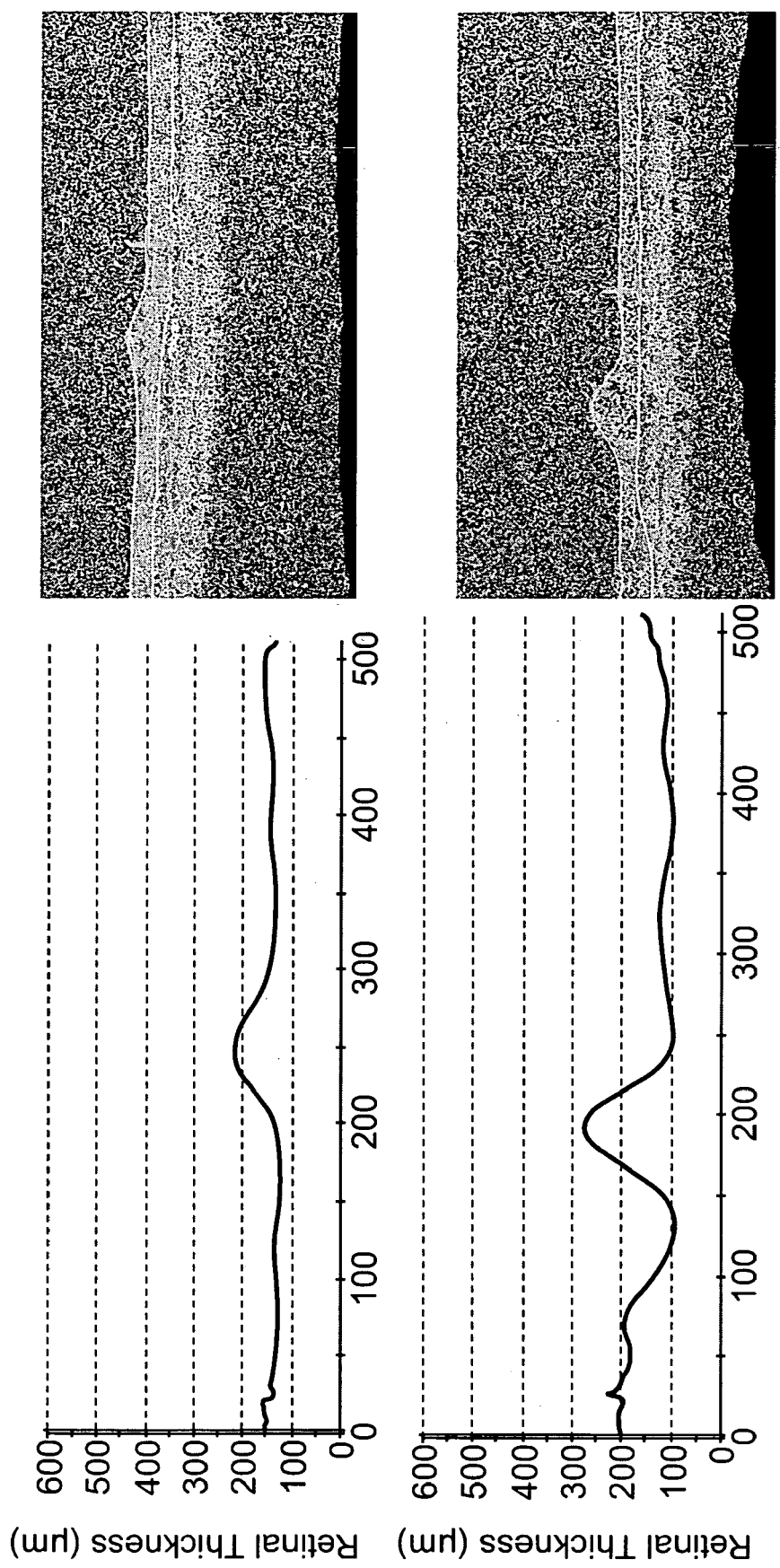
FIG. 3 shows a representative optical coherence tomography of the retinal thickness surrounding the implant site for two poly(caprolactone) (PCL) implants in accordance with embodiments of the invention, at 4 weeks after implant. Retinal surface (in μm) is represented on the X-axis, and retinal thickness (in μm) is represented on the Y-axis.

The topographical effect of using different implant diameters (150 µm vs. 320 µm) can also be seen in FIG. 3 by the comparative increase in retinal thickness at the site of the implant. No abnormalities were reported from increasing the implant diameter. An increase in the implant diameter merely resulted in a slightly more demanding surgical procedure and a larger area of cellular disruption.

Figure 4:
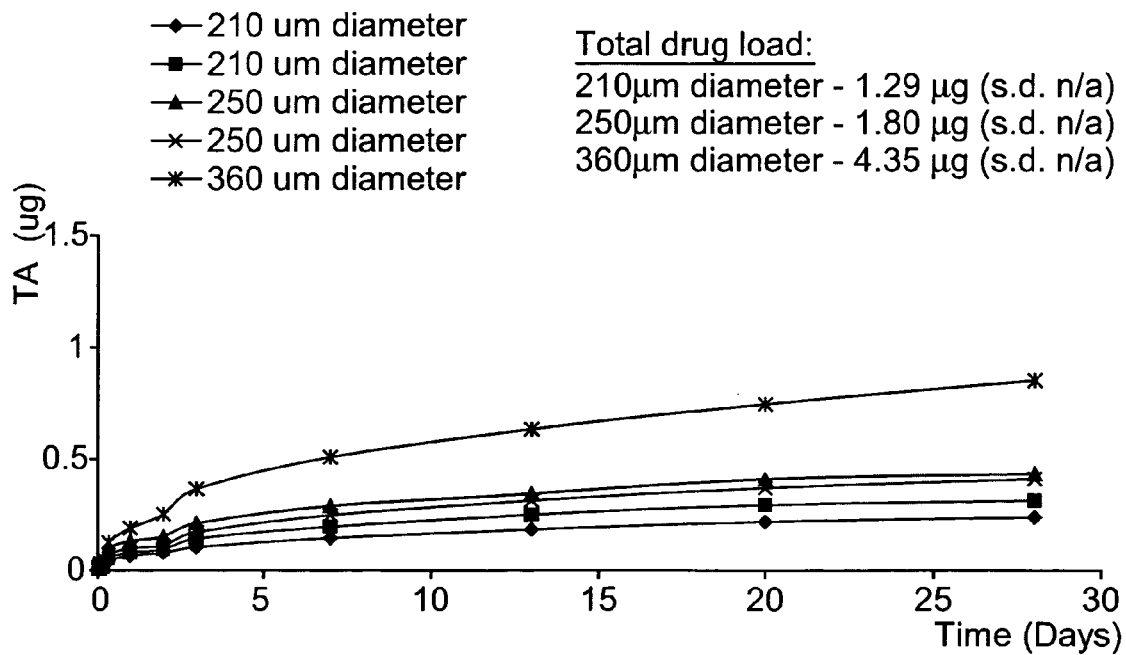
FIG. 4 shows a representative in vitro cumulative elution data for a 70:30 PCL/TA implant in accordance with one embodiment of the invention. In the graph, time (in days) is represented on the X-axis, while concentration of triamcinolone (TA, in μg) is represented on the Y-axis.
Figure 5:
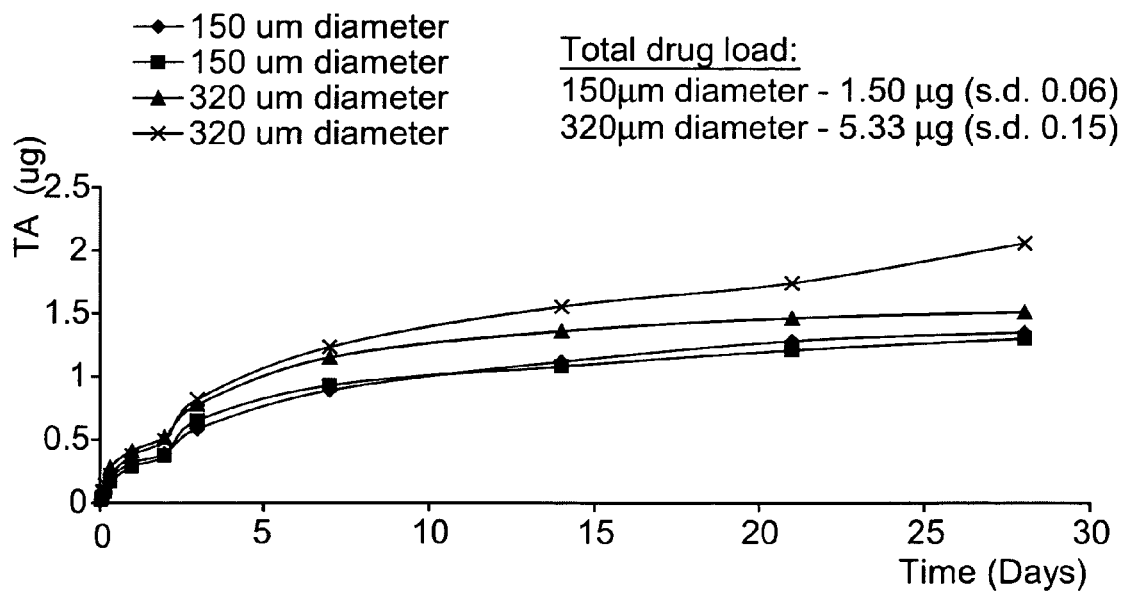
FIG. 5 shows a representative in vitro cumulative elution data for a 60:40 PCL/TA implant in accordance with one embodiment of the invention. In the graph, time (in days) is represented on the X-axis, while concentration of triamcinolone (TA, in μg) is represented on the Y-axis.
Figure 6:
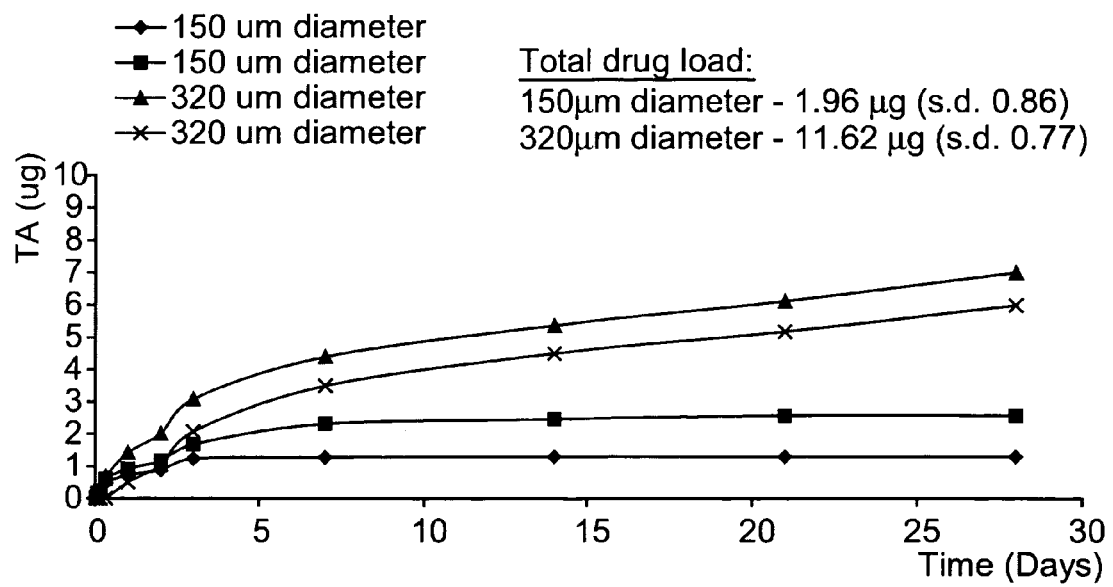
FIG. 6 shows a representative in vitro cumulative elution data for a 50:50 PCL/TA implant in accordance with one embodiment of the invention. In the graph, time (in days) is represented on the X-axis, while concentration of triamcinolone (TA, in μg) is represented on the Y-axis.

The in vitro elution rates for the different polymer-drug ratios and geometries into a BSS/BSA (1%) solution are shown in FIGS. 4-6. In general, the elution rates showed an early burst phase followed by a late first order phase. Without being bound by a particular theory, it is believed that the initial early rapid-release phase is attributed to the absorption of drug crystals in the surface to subsurface region of the implant into the medium, preceding diffusion from the polymer core. This initial burst may be particularly useful if it is desired to rapidly achieve local therapeutic dosage. For each of the different polymer-drug ratios, increasing the implant diameter or drug:polymer ratio resulted in an increase in the amount of drug eluted. Without being bound by theory, it is believed that this change results from the increased drug content and/or eluting surface area. For the larger (~300 µm) implants, increasing the ratio of drug in the formulation from PCL/TA 70:30 to 50:50 also increased the drug elution rate, while a drug dumping effect occurs if both the drug ratio is high (PCL/TA 50:50) and the implant diameter is small. In this latter case, total drug release had occurred during the initial burst, and the rate of TA absorption by the subretinal tissue was most likely a limiting factor. The near superimposition of all the elution profiles during the first few hours of each study also indicated that it was the rate of TA absorption that was the limiting step during the first stage of elution. Poly(caprolactone) is hydrophobic and impermeable to enzyme diffusion; therefore swelling, bulk diffusion, or degradation is unlikely in a bodily environment. Without intending to be bound by a particular theory, the TA elution profile that occurs after the initial surface to subsurface event is believed to be the result of a microporous drug boundary layer being formed and moving depper toward the core as the TA crystals are progressively absorbed by the body. As a result, the lower the drug loading, the smaller the polymer porosity formed during drug absorption and the lower the rate of TA elution.

Figure 7:
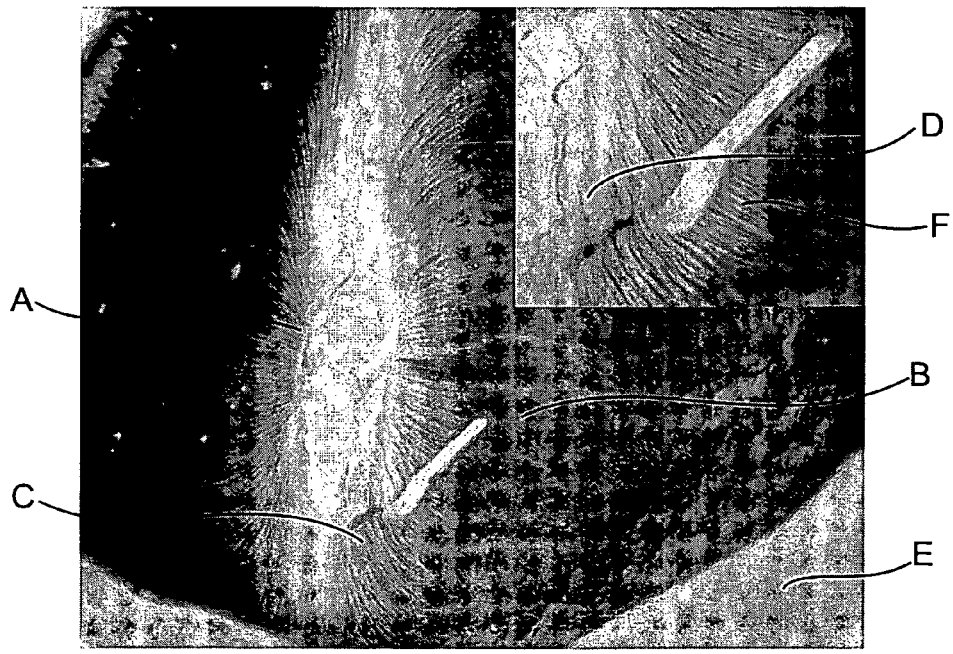
FIG. 7 shows a representative optical image and magnification of a subretinal PCL/TA implant in accordance with an embodiment of the invention, following 4 weeks implantation, where (7A) shows the optic nerve location; (7B) marks the implant location; (7C) and (7D) show the site of the retinotomy; (7E) is the outer sclera surface; and (7F) outlines the region of damage to the proximal end of the implant during micro forceps insertion.
Figure 8:
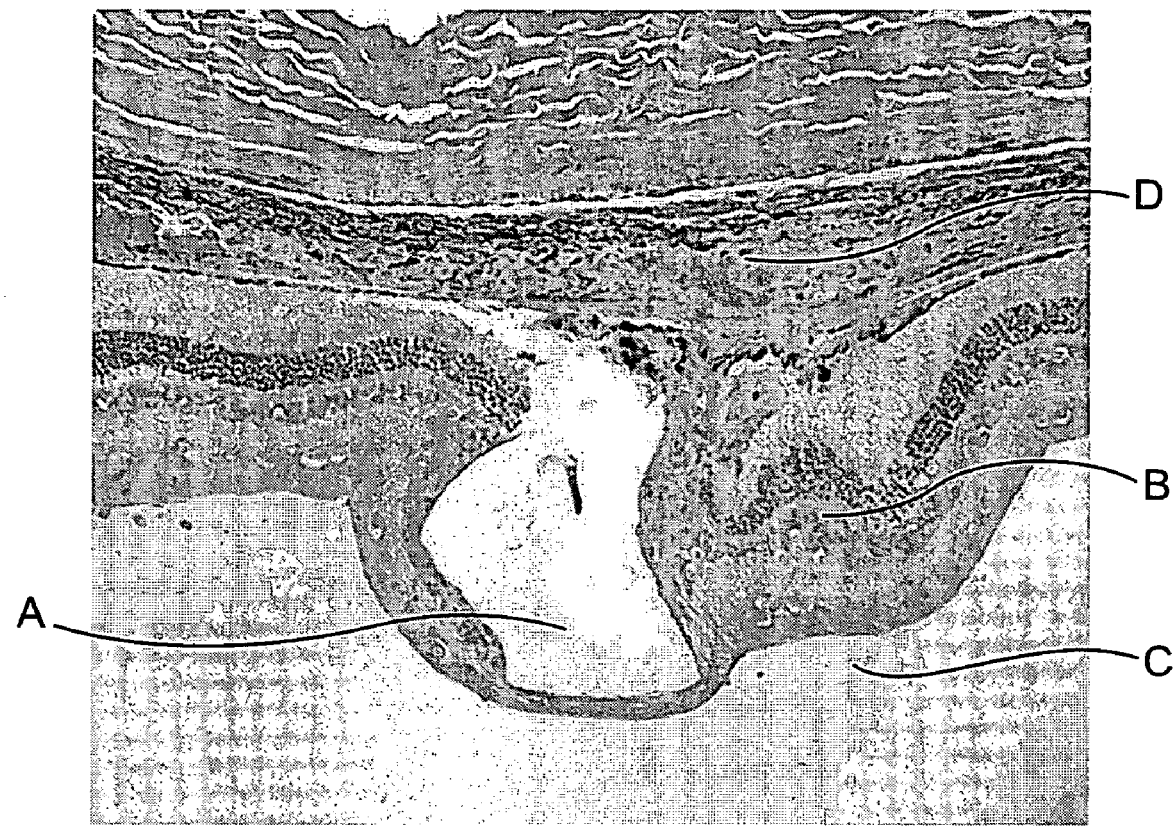
FIG. 8 shows histology (H&E staining) of a 150 μm PCL subretinal implant (no drug) in accordance with one embodiment of the invention, following 4 weeks implantation, where (8A) marks the device location; (8B) shows the RPE; (8C) shows the nerve fiber layer; (8D) shows the choroid; and (8E) shows the sclera.

The size of the retinotomy shown in the representative optical image FIG. 7 is less than 100 µm. Illustrative histology of implanted implants is shown in FIG. 8. However, smaller sized retinotomies are possible with the use of custom implantation tools.

Compared with the initial implant, the explanted implants at four weeks post surgery had a somewhat more fibrous polymer microstructure, than the initial implant. In some studies, only a flaky fibrous/porous polymer microstructure remained once the entire drug was extracted from the device during the in vitro elution studies. The molecular number selected for this polymer was at the high end ($M_w$, 80,000) of the commercially available range. PCL degrades by a reduction in $M_w$, so a longer degradation time is expected with this high $M_w$. There was no indication that polymer degradation had begun during the follow-up period.

Histology revealed that the implants, whether drug loaded or not, were encapsulated by one or two cell layers that did not appear fibrotic in nature, as shown in FIG. 8. The nerve fiber layer (ganglion axles) above the implant appeared intact, while the support cells immediately over the implant location are clearly absent in the PCL only implant and somewhat disrupted and thinned in the TA/PCL implanted eye. The Bruch's membrane appeared intact but there was evidence of thinning and disruption of the outer nuclear and RPE layers adjacent to the implant. Due to the lack of inflammatory response, PCL demonstrated excellent compatibility with this tissue region and the bulk of the observed cellular changes were attributed to the mechanical damage during the implantation. Other factors such as the impact of interfering with the nutritional source of these outer cellular layers may also play a role in these cellular changes.

It has been found that PCL degrades by random hydrolytic chain scission in subdermally implanted rabbits. The degradation initially manifests by a progressive reduction in molecular weight as the chain scission reactions propagate. However, it has also been shown that the physical weight of PCL does not change until the molecular weight has fallen to 5000—that is, there is no weight loss during the first phase of the degradation (Pitt C G. Poly ε caprolactone and its copolymers, In Chassin M Langer R, editors, *Biodegradable polymers as drug delivery systems*, New York: Dekker; 1990. p 71-119). Thus, phagocytosis and metabolism of small PCL fragments will not begin until the final phase of the degradation process. Further, PCL has shown excellent biocompatibility during the one-month follow up period.

The PCL/TA drug delivery system showed less disruption to the RPE layer and less tissue layer thinning in the adjacent regions of the implant than the PCL only implant, as shown in FIGS. 24 and 25. However, it is difficult to conclude whether this could be attributed to the anti-inflammatory effect of the steroid or was simply due to variability in surgical procedure and positioning. The region of retinal cell layers disruption where the implant resides extends for approximately 300 μm in width and 2000 μm in length. It has been found that the nerve fiber layer remains intact over the implant, but is disrupted at the site of the retinotomy. Thus, only a very focal region of vision loss is expected and one that is certainly less invasive than laser photocoagulation therapy.

Figure 9:
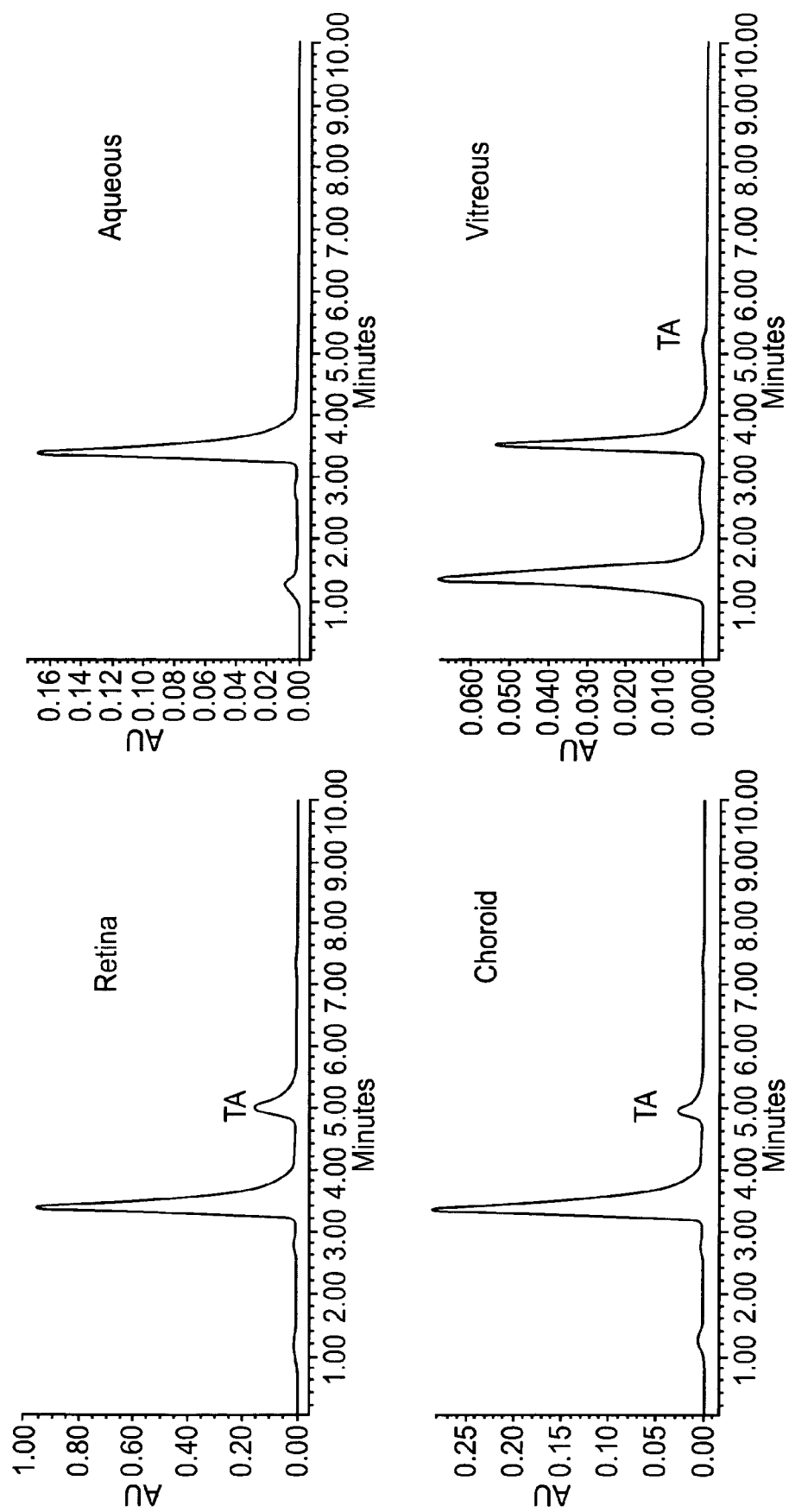
FIG. 9 shows a representative in vivo qualitative detection of triamcinolone acetonide (TA) following a 4-week subretinal implantation (PCL/TA 60:40) in accordance with one embodiment of the invention.

HPLC confirmed the presence of TA four weeks after the implant in the posterior tissue samples (FIG. 9). TA was not detected in the anterior structures or the blood. HPLC peaks for TA are marked on the graphs shown in FIG. 9. The additional peaks present indicate the internal standard prednisolone.

Based upon this initial investigation, it has been demonstrated that PCL has at least a one month elution capability with TA. Drug levels in the tissue were shown to be localized to the posterior eye segment. Histology showed no indication of inflammatory response from the presence of PCL. Minor mechanical damage from the insert was observed and is believed to be the leading cause of changes in the cellular layers and structures PCL encapsulation was also evident and is expected for implanted materials.

Description of Supporting FIGS.

FIG. 1 shows a representative fundus photography of an implanted poly(caprolactone)/triamcinolone acetonide (PCL/TA) implant in accordance with one embodiment of the invention, at 4 weeks after implant.

FIG. 2 shows a representative fluorescein angiography of an implanted PCL/TA implant in accordance with one embodiment of the invention, at 4 weeks after implant.

FIG. 3 shows a representative optical coherence tomography of the retinal thickness surrounding the implant site for two poly(caprolactone) (PCL) implants in accordance with embodiments of the invention, at 4 weeks after implant. Retinal surface (in μm) is represented on the X-axis, and retinal thickness (in μm) is represented on the Y-axis.

FIG. 4 shows a representative in vitro cumulative elution data for a 70:30 PCL/TA implant in accordance with one embodiment of the invention. In the graph, time (in days) is represented on the X-axis, while concentration of triamcinolone (TA, in μg) is represented on the Y-axis.

FIG. 5 shows a representative in vitro cumulative elution data for a 60:40 PCL/TA implant in accordance with one embodiment of the invention. In the graph, time (in days) is represented on the X-axis, while concentration of triamcinolone (TA, in μg) is represented on the Y-axis.

FIG. 6 shows a representative in vitro cumulative elution data for a 50:50 PCL/TA implant in accordance with one embodiment of the invention. In the graph, time (in days) is represented on the X-axis, while concentration of triamcinolone (TA, in μg) is represented on the Y-axis.

FIG. 7 shows a representative optical image and magnification of a subretinal PCL/TA implant in accordance with an embodiment of the invention, following 4 weeks implantation, where (7A) shows the optic nerve location; (7B) marks the implant location; (7C) and (7D) show the site of the retinotomy; (7E) is the outer sclera surface; and (7F) outlines the region of damage to the proximal end of the implant during micro forceps insertion.

FIG. 8 shows histology (H&E staining) of a 150 μm PCL subretinal implant (no drug) in accordance with one embodiment of the invention, following 4 weeks implantation, where (8A) marks the device location; (8B) shows the RPE; (8C) shows the nerve fiber layer; (8D) shows the choroid; and (8E) shows the sclera.

FIG. 9 shows a representative in vivo qualitative detection of triamcinolone acetonide (TA) following a 4-week subretinal implantation (PCL/TA 60:40) in accordance with one embodiment of the invention.

Example 2

All procedures abided by the Guide for the Care and Use of Laboratory Animals, the USDA Animal Welfare Regulations (CFR 1985) and Public Health Service Policy on Humane Care and Use of Laboratory Animals (1996) and the Institution's policies governing the use of vertebrate animals for research, testing, teaching or demonstration purposes.

Seven pigmented rabbits (J1-J7) underwent standard pars plana vitrectomy, and insertion of a drug delivery device into the subretinal space. The animals were anesthetized with an intramuscular injection of 0.3 mL of ketamine hydrochloride (100 mg/mL; Fort Dodge Lab., Fort Dodge, Iowa) and 0.1 mL of xylazine hydrochloride (100 mg/mL; Miles Inc, Shawnee Mission, Kans.) per kilogram of body weight. Pupils were dilated with 1 drop each of 2.5% phenylephrine and 1% tropicamide. A 3-mm peritomy was made at the superotemporal and superonasal quadrant of the right eye. Sclerotomies were created with a 20-gauge microvitreoretinal blade 1 to 2 mm posterior to the limbus in the superotemporal and superonasal quadrants. An infusion pipe line was inserted through the superonasal sclerotomy and a vitreous cutter (Bausch & Lomb, St Louis, USA) was inserted through the superotemporal sclerotomy. The vitreous cutter and infusion pipe were used to perform a 2-port core vitrectomy. The illumination provided by the operating microscope (Zeiss, Germany) was sufficient for the operation. Using intraocular microscopic forceps (Bausch & Lomb, St Louise, USA) the drug delivery implant was inserted in the subretinal space creating a small retinotomy. The bevel shaped tip of the implant facilitated insertion into the subretinal space. The implant was left in position and the forceps was withdrawn from the eye. No laser retinopexy was applied to seal the retinal breaks. The infusion line was removed and the sclerotomies and conjuctival openings were closed using Vycril 7-0 (Ethicon, USA).

TABLE 2 outlines certain experimental variables. TABLE 3 summarizes experimental results obtained.

TABLE 2

| Rabbit | Total Duration | Follow-Up | Implant | Procedure |
|---|---|---|---|---|
| J1 | 2 days | 2 days | PCL/TA | No bleb |
| J1 | 2 days | 2 days | Polymer drug coated/TiNi alloy core | No bleb |
| J2 | 1 week | 2 days/1 week | PCL/TA | No bleb |
| J2 | 1 week | 2 days/1 week | Polymer drug coated/TiNi alloy core | No bleb |
| J3 | 2 weeks | 1 week/2 weeks | PCL | No bleb |
| J3 | 2 weeks | 1 week/2 weeks | TiNi alloy core | No bleb |
| J4 | 2 weeks | 1 week/2 weeks | PCL/TA | No bleb |
| J4 | 2 weeks | 1 week/2 weeks | Polymer drug coated/TiNi alloy core | No bleb |
| J5 | 2 weeks | 1 week/2 weeks | PCL/TA | Bleb |
| J6 | 2 weeks | 1 week/2 weeks | PCL/TA | Bleb |
| J7 | 2 weeks | 1 week/2 weeks | Polymer drug coated/TiNi core | Beb |

TABLE 3

| Rabbit | Lens Touch | Retinal Hemorrhage | Leekage 2 days | Leekage 1 week | Leekage 2 weeks | Fully Implanted | Partially Implanted |
|---|---|---|---|---|---|---|---|
| J1 | No | No | Yes | — | — | No | Yes |
| J1 | No | No | Yes | — | — | No | Yes |
| J2 | No | Yes | Yes | No | — | Yes | No |
| J2 | No | Yes | Yes | No | — | Yes | No |
| J3 | Yes | No | — | — | — | — | — |
| J3 | Yes | No | — | — | — | — | — |
| J4 | No | No | — | No | No | Yes | No |
| J4 | No | No | — | No | No | No | Yes |
| J5 | No | No | — | No | No | Yes | No |
| J6 | No | No | — | No | No | Yes | No |
| J7 | No | No | — | — | No | Yes | No |

Comments:

Clinical examination using slit-lamp and indirect ophthalmoscopy did not indicate any adverse inflammatory response from the presence of TiNi alloy, polymer drug coated/TiNi alloy core, PCL/TA, and PCL implants during the follow-up period.

A lens touch occurred during Rabbit J3 implantation and a cataract formation was reported from one week post-op onwards. The vitreous opacity and cataract present in Rabbit J3 during the first week post-op made its early data collection difficult to interpret. A vitreous opacity of unknown etiology was present in Rabbit J7 at one week post-op, but completely receded by week two.

Fluorescein angiography showed the presence of vascular leakage in Rabbit J1 and Rabbit J2 at 2 day post-op. Rabbit J1 was sacrificed at 2 day post op for histology data. The leakage subsided in Rabbit J2 by 1 week post op. Vascular leakage was anticipated in Rabbit J1 from the level of implant trauma sustained by the multiple retinotomy attempts during the initial learning curve. Vascular leakage was not observed in Rabbits J3, J4, J5, J6 and J7 at 1 and 2 weeks post-op.

The polymer drug coated/TiNi alloy core implant implanted in Rabbit J7 was cut to a length of approximately 2.25 mm. This particular geometry was found to avoid a final resting position across multiple retinal tissue layers. It is believed the similar geometries, slightly greater than and less than this length, with an upper desired range of approximately 3 mm, will also avoid a final resting position across multiple retinal tissue layers. As the implant gets shorter in length, it may be more difficult to handle the implant for proper insertion and positioning and, further, the amount of therapeutics/agents which may be contained in the insert may be limited.

Example 3

Materials Used and Abbreviations

Core:
NIT: 80 μm etched Nitinol wire, commercially available from Nitinol Devices and Components (Freemont Calif.).
Bioactive Agent:
RAP: Rapamycin, commercially available from LC Laboratories, Woburn Mass.
Polymers:
pEVA: polyethylene vinyl acetate copolymer (33% wt. vinyl acetate and 67% wt. polyethylene), commercially available from Aldrich Chemical Co.
pBMA: poly(n-butyl methacrylate), commercially available from Aldrich Chemical Co.
Solvent:
$CHCl_3$: chloroform solvent, commercially available from Burdick & Jackson.
Implant Preparation:
Coating Solution Preparation:

A coating solution was prepared by first adding 25.0 parts pEVA and 25.0 parts pBMA to an aliquot of $CHCl_3$ solvent. In order to dissolve the pEVA, the components were heated to 30° to 40° C. for approximately 1 hour. After the pEVA and pBMA had dissolved in the $CHCl_3$, the resulting polymer/solvent solution was allowed to cool to room temperature. Then, 50 parts of RAP was added to the polymer/solvent solution and the RAP was stirred into the polymer/solvent solution at room temperature for approximately 30 minutes to form a coating solution. The resulting coating solution was filtered using a 10 μm polypropylene filter (Gelman Sciences pall membrane Part No. 61756). The final coating solution contained about 40 mg/ml of solids (i.e., pEVA, pBMA, and RAP).
Coating Procedure:

NIT wire was cut into lengths of approximately 1 cm each using a scissors. The wire lengths were cleaned with a wipe (Alpha Wipe from Tex Wipe) that had been dampened with isopropyl alcohol. Each wire length was then weighed to +/−0.003 μg using a microbalance (Type UMX2, from Metler-Toledo).

The coating solution was sprayed onto the NIT wire using ultrasonic coater equipment that consisted of an ultrasonic spray head (Sono-Tek, Milton, N.Y.) and syringe pump system for the coating solution. A cylindrical pin vise was used to hold the end of the NIT wire. The NIT wire was held perpendicular to the spray head at the focal point of the spray (i.e., about 2-3 mm from the spray head) and was rotated at about 200 rpm. The spray head was moved longitudinally over the NIT wire to apply the coating composition. A grid-like pattern as shown in FIG. 57 was used for the coating with 0.1 mm longitudinal movements. The coating was dried by evaporation of the solvent at room temperature (approximately 20° C. to 22° C.) overnight. The resulting coating was about 3.0 mm in total length, comprising a center portion of about 2.0 mm in length having a uniform thickness of about 300 µm, and two segments of about 0.5 mm in length with transitional thickness on each side of the center portion. After drying, the coated NIT wire was weighed to +/−0.003 µg using a microbalance (Type UMX2, from Metler-Toledo). The implant coating weight was calculated by subtracting the weight of the uncoated wire from the final weight of the coated wire. The total amount of RAP in each implant was calculated by multiplying the coating weight by 0.50, which represents the weight percent of RAP in the coating. The total amount of RAP in the polymer coating of the implant ranged from 26 to 89 µg (see, Table 4).

Prior to implanting in rabbits, the implants were trimmed to a length of between about 2.3 to 3.04 mm (see, Table 4).

Implantation:

Experiments were conducted in accordance with the ARVO Statement for the Use of Animals in Ophthalmic and Visual Research.

Six Dutch pigmented rabbits were given general anesthesia by an intramuscular injection of 1-1.5 mL of a 4:1 mixture of ketamine hydrochloride (100 mg/mL; Fort Dodge Labs, Fort Dodge, Ind.) and xylazine hydrochloride (100 mg/mL; Miles, Inc., Shawnee Mission, Kans.).

In all rabbits, surgery was performed on the right eye only. Pupillary dilation was achieved with topical 1% tropicamide and 2.5% phenylephrine. After limited conjunctival peritomy in the superior quadrant, stab incisions were made approximately 1 mm posterior to the limbus using a 20-gauge microvitreoretinal blade. In three rabbits (RS1, RS3 and RS4) no vitrectomy was performed. A vitreoretinal microforceps was used to grasp the end of an implant, and it was introduced into the posterior chamber through the sclerotomy. The tip of the implant was used to puncture the retina several millimeters inferior to the disc and the vascular arcades. The forceps were then used to slide the implant into the subretinal space through this retinotomy.

In three rabbits (RS3, RS5, and RS6), a vitrectomy was performed prior to implant insertion. In these eyes, one sclerotomy was created superiorly and another superonasally. An infusion cannula was inserted through the superonasal sclerotomy and sutured into place. A vitreous cutter was introduced through the superior sclerotomy. After completion of a core vitrectomy, the vitrector was removed from the eye. In two of the rabbits having a vitrectomy (RS5 and RS6), a 25-gauge needle was used to puncture the retina several millimeters inferior to the disc and the vascular arcades and raise a small subretinal bleb by injecting approximately 0.1 mL of balanced salt solution into the subretinal space. With the microforceps, the implant was then inserted through the retinotomy into the subretinal space in this location. In one of the rabbits (RS3) no subretinal bleb was raised; rather, the implant was inserted directly beneath the retina after vitrectomy in the manner described above.

In all rabbits, after the implant had been inserted, the instruments were removed from the eye, and the sclerotomies were closed with 7-0 Vicryl sutures (Johnson and Johnson, Piscataway, N.J.). The conjunctiva was left to close by secondary intention. Subconjunctival injection of gentamicin (0.2 mL of 40 mg/mL solution) was performed.

Monitoring and Evaluation:

Indirect ophthalmoscopic examination, fundus photography, fluorescein angiography, and optical coherence tomography were performed on the right eye of each rabbit at 1, 2, and 4 weeks post-operatively. After the week 4 studies were completed, the rabbits were euthanized with an intracardiac injection of sodium pentobarbital (Anpro Pharmaceuticals, Arcadia, Calif.). The right eye of each rabbit was enucleated and placed in 4% paraformaldehyde for 24 hours. The eyes were then transferred to Dulbecco's phosphate buffered saline for storage at 4° C. until further dissection, at which time they were sectioned down to a 2 cm×2 cm block of the retina-choroid-sclera complex at the posterior pole. This was embedded in paraffin, sectioned, and stained with hematoxylin and eosin using standard techniques.

Implantation Results:

Implants were implanted into the subretinal space in three rabbits and into the sub-RPE space in one rabbit. (Table 4) In four eyes (RS1-RS4), no bleb of subretinal fluid was raised prior to implantation of the implant. In these cases, there was one subretinal Implantation (RS1), one sub-RPE implantation (RS3), and two unsuccessful attempts at implantation. In two cases (RS5 and RS6), a bleb of subretinal fluid was raised before implant placement. In both of these instances, the implant was inserted into the subretinal space without difficulty.

The presence or absence of the vitreous body over the area of implantation was found to be a factor determining the ease of the procedure. In one of the cases in which no vitrectomy was performed (RS1), the surgeon was able to insert the implant into the subretinal space, and the implant remained in place upon removal of the forceps. However, two rabbits (RS2 and RS4), both of which did not undergo vitrectomy prior to implant implantation, were sacrificed at the time of surgery because of the creation of multiple retinotomies during attempted implantation. In these two cases, the vitreous body prevented successful implantation by adhering to the implant and causing it to egress from the subretinal space when the implantation forceps were withdrawn. By contrast, when a vitrectomy had been performed prior to implantation (RS3, RS5, and RS6), it was possible to release the implant and withdraw the forceps without disturbing the position of the device.

Tolerance of Implant Implants in the Rabbit Eye:

All scheduled follow-up exams were completed over a one-month time period for three of the four rabbits that received implants (RS1, RS3, and RS5). In one rabbit (RS6), posterior synechiae developed between weeks 1 and 2, so adequate pupillary dilation could not be achieved on the follow-up exams at weeks 2 and 4. Consequently, fluorescein angiography (FA) and optical coherence tomography (OCT) studies could not be performed at these visits. No retinal detachment occurred in any of the four eyes that received implants.

In three rabbits (RS1, RS3, and RS5), no signs of inflammation or toxicity were detected on follow-up examination. In addition, the implants did not migrate from their initial implantation sites. In RS1, in which no bleb of subretinal fluid was raised prior to device insertion, at week 1 small amounts of residual subretinal hemorrhage from the procedure were still present adjacent to the implant, causing blockage on fluorescein angiography. This resolved with time, so that less blockage from subretinal hemorrhage was noted at week 2 and none by week 4. The angiogram otherwise showed only blockage by the device. OCT also confirmed the subretinal location of the device. There was no evidence of atrophy or damage to adjacent retina or RPE. In RS5, in which a bleb of subretinal fluid was raised to assist with correct subretinal device placement, there was no subretinal hemorrhage noted at any time point. Fluorescein angiography showed a linear hypofluorescent spot inferior to the device that was the site of instrument touch during surgery. In addition, mild hypopigmentation could be seen around the device, corresponding to the area in which the subretinal bleb had been raised. This circular area appeared mildly hyperfluorescent on angiography. There was no indication of other damage to adjacent tissue by the implant.

In RS6, exams at weeks 1 and 2 showed that the implant remained stable at the site of implantation, and the adjacent tissue appeared normal. Mild anterior chamber inflammation and posterior synechiae developed by week 2, so pupillary dilation was impaired, making photography difficult. Indirect ophthalmoscopy showed no evidence of posterior chamber inflammation.

In RS3, in which the device was implanted beneath the RPE, the implant also remained in a stable position and did not cause any visible abnormalities of adjacent areas. The implant could not be directly visualized on examination, but angiography showed blockage by it, and OCT appeared to corroborate its location.

Histology Results:

In eyes in which the implant was implanted subretinally, sections of the posterior pole at the implantation site showed loss of photoreceptors overlying the device. Adjacent structures appeared normal.

TABLE 4

Implant Characteristics and Results

| Rabbit No. | Vitrectom | Bleb | Implant Length (mm) | Total RAP Content (ug) | Outcome |
|---|---|---|---|---|---|
| RS1 | No | No | 2.3 | 28 | Subretinal Implantation |
| RS2 | No | No | 3.04 | 61.5 | Sacrificed |
| RS3 | Yes | No | 2.54 | 88.5 | Sub-RPE Implantation |
| RS4 | No | No | 2.88 | 28 | Sacrificed |
| RS5 | Yes | Yes | 2.7 | 26 | Subretinal Implantation |
| RS6 | Yes | Yes | 2.46 | 89 | Subretinal Implantation |

Example 4

Materials and Abbreviations

Core Materials:
NIT: 80 um etched Nitinol wire, obtained from Nitinol Devices and Components (Fremont, Calif.).
PMMA: poly(methyl methacrylate) polymer, obtained from Biogeneral Inc. (San Diego, Calif.).
CG: chromic gut, obtained from Ethicon (Somerville, N.J.).
Polymers:
pEVA: polyethylene vinyl acetate copolymer (33% wt. vinyl acetate and 67% wt. polyethylene), commercially available from Aldrich Chemical Co.
pBMA: poly(n-butyl methacrylate), commercially available from Aldrich Chemical Co.
Solvents:
$CHCl_3$: chloroform solvent, commercially available from Burdick & Jackson.
THF: tetrahydrofuran solvent, commercially available from Burdick & Jackson.

Bioactive Agents:
RAP: rapamycin, commercially available from LC Laboratories, Woburn Mass.
TA: triamcinolone acetonide, commercially available from PfizerCenterSource, Kalamazoo, Mich.
Implant Preparation:
TA Coating Solution Preparation (Coating Solution 1):

A coating solution was prepared by first adding 22.5 parts pEVA and 27.5 parts pBMA to an aliquot of THF solvent. In order to dissolve the pEVA, the components were heated to 30° to 40° C. for approximately 1 hour. After the pEVA and pBMA had dissolved in the THF, the resulting polymer/solvent solution was allowed to cool to room temperature. Then, 50 parts of TA was added to the polymer/solvent solution and the TA was stirred into the polymer/solvent solution at room temperature for approximately 30 minutes to form a coating solution. The resulting coating solutions were filtered using a 10 µm polypropylene filter (Gelman Sciences pall membrane Part No. 61756). The final coating solutions contained about 60 mg/ml of solids (i.e., pEVA, pBMA, and TA).

RAP Coating Solution Preparation (Coating Solution 2):

A coating solution was prepared by first adding 10 parts pEVA and 30 parts pBMA to an aliquot of $CHCl_3$ solvent. In order to dissolve the pEVA, the components were heated to 30° to 40° C. for approximately 1 hour. After the pEVA and pBMA had dissolved in the $CHCl_3$, the resulting polymer/solvent solution was allowed to cool to room temperature. Then, 60 parts of RAP was added to the polymer/solvent solution and the RAP was stirred into the polymer/solvent solution at room temperature for approximately 30 minutes to form a coating solution. The resulting coating solution was filtered using a 10 µm polypropylene filter (Gelman Sciences pall membrane Part No. 61756). The final coating solution contained about 40 mg/ml of solids (i.e., pEVA, pBMA, and RAP).

pBMA Coating Solution Preparation (Coating Solution 3):

A coating solution was prepared by first adding pBMA to an aliquot of $CHCl_3$ solvent. In order to dissolve the pBMA, the components were stirred for approximately 3 hours at room temperature. The resulting coating solution was filtered using a 10 µm polypropylene filter (Gelman Sciences pall membrane Part No. 61756). The final coating solution contained about 10 mg/ml of pBMA.

Coating Procedure:

The core materials were cut into lengths of approximately 1 cm each using a scissors. The cores were cleaned with a wipe (Alpha Wipe from Tex Wipe) that had been dampened with isopropyl alcohol. Each core was then weighed to +/−0.003 µg using a microbalance (Type UMX2, from Metler-Toledo).

The coating solutions were sprayed onto the core lengths using ultrasonic coater equipment that consisted of an ultrasonic spray head (Sono-Tek, Milton, N.Y.) and syringe pump system for the coating solution. A cylindrical pin vise was used to hold the end of the cores. The core was held perpendicular to the spray head at the focal point of the spray (i.e., about 2-3 mm from the spray head) and was rotated at about 200 rpm. The spray head was moved longitudinally over the core to apply the coating composition. A grid-like pattern as shown in FIG. 57 was used for the coating with 0.1 mm longitudinal movements. The coatings were dried by evaporation of the solvent at room temperature (approximately 20° C. to 22° C.) overnight. For RAP slow release formulations, an additional coating consisting of pBMA dissolved in $CHCl_3$ (Coating Solution 3) was sprayed over the dried RAP/pEVA/pBMA coating. The coating was dried by evaporation of the solvent at room temperature (approximately 20° C. to 22° C.) overnight. The resulting implants were weighed to +/−0.003 μg using a microbalance (Type UMX2, from Metler-Toledo).

The implants comprising TA (prepared from Coating Solution 1) had coatings that were about 2 mm in total length, comprising a center portion of about 1 mm in length having a uniform thickness of about 250 μm, and two segments of about 0.5 mm in length with transitional thickness on each side of the center portion.

The implants comprising RAP (prepared from Coating Solution 2, and Coating Solution 3 (RAP slow release)) had coatings that were about 2.5 mm in total length, comprising a center portion of about 1.5 mm in length having a uniform thickness of about 350 μm, and two segments of about 0.5 mm in length with transitional thickness on each side of the center portion.

The implants included a tail section of uncoated core material of about 1 mm in length to provide a handling region for docking with ophthalmic surgical instrumentation. This also prevented any damage to the eluting segment of the platform during implantation.

Prior to implanting, the implants were sterilized by ethylene oxide gas.

Implantation:

All participating investigators abided by the policies described in the Guidelines for the Care and Use of Laboratory Animals, the OPRR Public Health Service Policy on the Humane Care and Use of Laboratory Animals (revised 1986), the U.S. Animal Welfare Act, as amended, and the Institution's and the Association for Research in Vision and Ophthalmology's (ARVO) policies governing the use of vertebrate animals for research, testing, teaching or demonstration purposes.

Pupils were fully dilated before implantation with 1 drop each of cyclopentolate hydrochloride 1% (Bausch & Lomb, Rochester, N.Y.) and phenylephrine hydrochloride 5% (Bausch & Lomb). The rabbits were anesthetized by intramuscular injection of 0.3 mL of ketamine hydrochloride (100 mg/mL; Fort Dodge Labs, Fort Dodge, Ind.) and 0.1 mL of xylazine hydrochloride (100 mg/mL; Miles, Inc., Pittsburgh, Pa.) per kilogram of body weight. A periocular surgical prep was performed by swabbing the area using a 1:10 dilution of povidone iodine in saline. The surface of the eye was prepped with a 1:20 dilution of povidone iodine in saline. The rabbit was positioned under the operating microscope and draped. A wire lid speculum was placed.

A 3-mm peritomy was made at the superotemporal and superonasal quadrant of the right eye. Sclerotomies were created with a 20-gauge microvitreoretinal blade, 1 to 2 mm posterior to the limbus in the superotemporal and superonasal quadrants. An infusion line was inserted and sutured through the superonasal sclerotomy, and a vitreous cutter was inserted through the superotemporal sclerotomy. A two-port core vitrectomy was performed, with illumination provided by the operating microscope (Carl Zeiss Ophthalmic Systems, Inc.). Intraocular microscopic forceps were used to insert the drug delivery implant in the subretinal space, as documented by Table 5. The feathered shape and semi-rigid structure of the implant allowed easy insertion. The implant was left in position and the forceps were withdrawn from the eye. No laser retinopexy was applied to seal the retinal breaks. The infusion line was removed, and the sclerotomies and conjunctival openings were closed using Vycril 7-0 (Ethicon). At the conclusion of surgery, a subconjunctival injection of antibiotic, 0.1 cc of 40 mg/ml gentamycin (Phoenix Scientific, St. Joseph, Mo.) and 0.1 cc of 2 mg/ml dexamethasone (Phoenix Scientific) was administered away from the surgery site. Erythromycin antibiotic ointment (Eli Lilly & Co., Indianapolis. Ind.) was applied daily to the operated eye for 2 days following the procedure. Buprenex (Reckitt Benckiser, Richmond Va.) was given daily for two days. Harlan High Fiber Rabbit Diet #2031 was provided daily. Water was provided ad libitum and delivered through an automatic watering system. Animals were individually housed in suspended stainless steel cages identified by a card indicating the lab number, investigator, animal number, test code, sex, and date received. The light cycle was controlled using an automatic timer (12 hours light, 12 hours dark).

Complete ophthalmic examinations using indirect ophthalmoscopy and a 20-diopter lens (Vantage Indirect Ophthalmoscope, Keeler Ltd., Windsor, England) were performed at baseline and 1, 2, and 4 weeks postoperatively. Before each examination, animals were anesthetized with an intramuscular injection of 0.3 mL of ketamine hydrochloride (100 mg/mL) and 0.1 mL of xylazine hydrochloride (100 mg/mL) per kilogram of body weight. Pupils were fully dilated with 1 drop each of cyclopentolate hydrochloride 1% (Bausch & Lomb) and phenylephrine hydrochloride 5% (Bausch & Lomb). A speculum was used to part the rabbit's eye lids. The clinical examination progressed from a macroscopic superficial evaluation to a detailed indirect ophthalmoscopic examination of the posterior and anterior structures. Fundus photography (Zeiss FF 450plus IR Fundus Camera with VISUPAC/System 451) and optical coherence tomography (OCT III, Carl Zeiss Ophthalmic Systems, Inc.) were used to document each case and any specific findings. The conjunctiva was visually examined for redness, chemosis, thinning, lesions, fibrous growth, and discharge. The cornea was examined for signs of neovascularization, ulceration and edema. The lens was inspected for cataract formation and further evaluated with respect to any lens touch that may have occurred during the implantation. The presence of any flare or cells in the anterior chamber or changes in pupillary shape was also noted. The iris was examined for vascular hyperemia, rubeosis iridis, swelling and synechia. The vitreous was examined for hemorrhage and inflammatory debris. The retina was examined for any lesions, tears, detachments or hemorrhage. Any extrusion or migration of the implant was also assessed.

Results:

Subretinal drug-delivery implants were surgically implanted into the right eye (OD) of 20/24 rabbits, according to Table 5. The design and geometry of the implant was optimized over several prototyping studies. The optimal length of penetration into the retina was 2.75 mm. Penetration lengths greater than this resulted in an increase in hemorrhagic complications. Four of 24 rabbits were sacrificed during early surgery: three because of surgical complications involving the infusion-line flow-rate equipment, leading to retinal detachment from fluid pooling, and one because of an uncontrollable retinal hemorrhage caused by blunt instrument trauma. A tail was included in the implant design to allow convenient gripping with standard intraocular microforceps. The surgical procedures, performed by three vitreoretinal surgeons, were relatively short in duration, with each surgery lasting less than 15 minutes from the point at which the anesthetic began to take effect. Intraocular lens touch occurred in six rabbits, and a lensectomy was subsequently performed in four of the six to clear a visual path to the fundus. A focal cataract developed in the two rabbits that did not undergo a lensectomy. While rabbit and human eyes share several important structural features, the rabbit lens is harder to avoid because of its substantially larger size and posterior position.

No rabbits were sacrificed at any of the postoperative follow-up points. All remained in good general health throughout the study. Follow-up clinical examinations at 1, 2 and 4 weeks reflected good implant biocompatibility and a lack of serious surgical complications in both the control and the triamcinolone acetonide implant groups. One day after operation, all eyes exhibited slight conjunctival redness from the surgery and suturing. By 1 week post-op, conjunctival redness had dissipated in all but four animals. By 2 weeks post-op, conjunctival redness had dissipated in all animals. By 1 week post-op, one rabbit developed a corneal neovascularization and edema from excessive paw scratching. By 1 week post-op, three rabbits developed corneal edema from excessive paw scratching. All cases resolved by 2 weeks post-op with lubricants, prophylactic antibiotic ointments and an anti-scratching neck brace. No permanent corneal scarring or opacity resulted. These rabbits had undergone a lensectomy during surgery and were therefore subjected to additional trauma. There were no signs of conjunctival edema, thinning, fibrous tissue growth, or conjunctival lesions. Clinical examination at 1, 2, and 4 weeks showed no detectable accumulation of subretinal fluid, exudates or fibrosis surrounding the device at any of the follow-up points. Localized retinal hemorrhage was noted in five rabbits at the completion of surgery, most likely from damage to the retinal pigment epithelium during implantation. This regressed to three rabbits by the completion of the study. Fundus examination revealed no retinal tears other than that noted during the surgical procedure from the retinotomy and, in some cases, instrument trauma. Fundus photography showed that the implant maintained its position with no signs of inflammation or migration. Optical coherence tomography revealed successful placement of the implant in the subretinal space of all the rabbit eyes.

Figure 20:
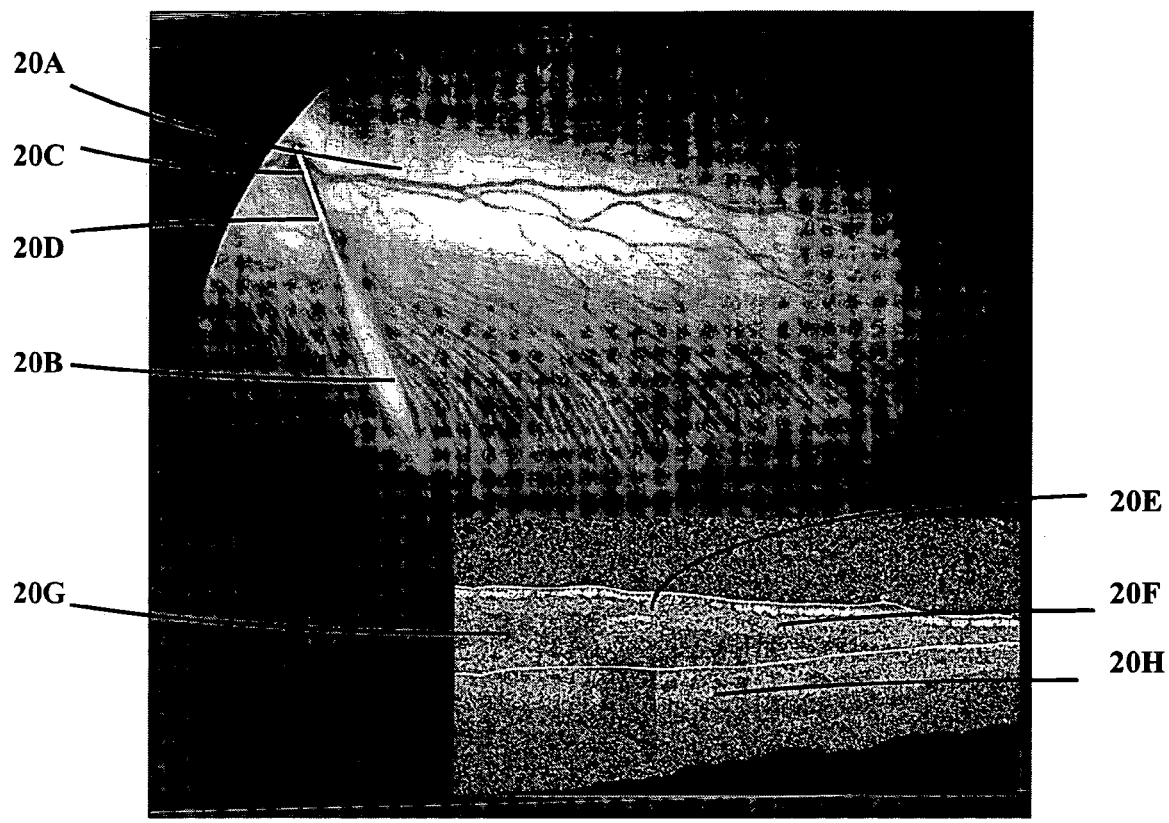
FIG. 20 shows a a representative fundus photograph and optical coherence tomography of a single TiNi core subretinal implant loaded with triamcinolone acetonide at four weeks implantation, where (20A) marks the optic nerve; (20B) marks the subretinal implant; (20C) shows the site of the retinotomy; (20D) marks the implant tails that are located periretinal; (20E) marks the cross sectional depth location of the implant using optical coherence tomography; (20F) shows the RPE and nerve fiber layer; (20G) is a local retinal detachment surrounding the implant; and (20H) is the choroid.
Figure 21:
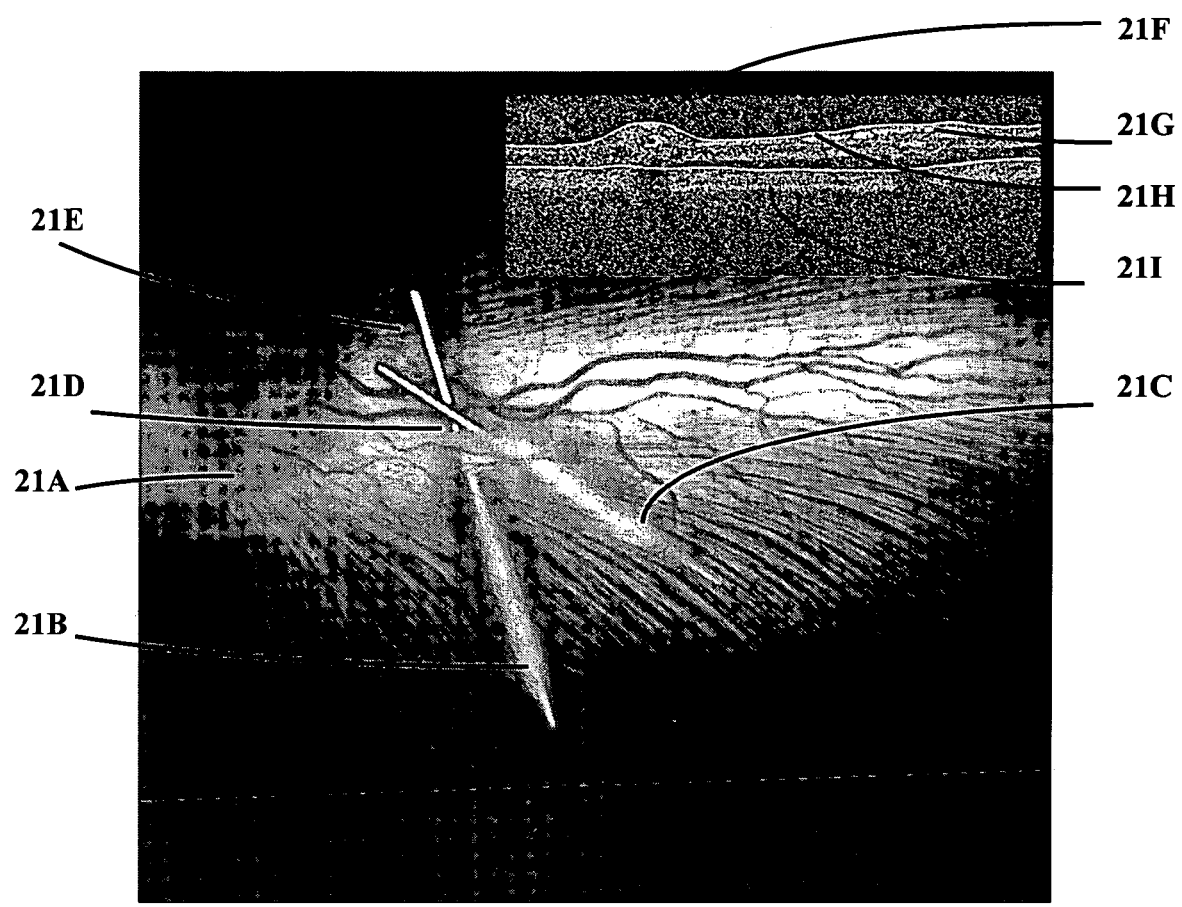
FIG. 21 shows a representative fundus photograph and optical coherence tomography of a double TiNi core subretinal implant loaded with triamcinolone acetonide at one week implantation, where (21A) marks the optic nerve; (21B) and (21C) mark the subretinal implants; (21D) shows the site of the retinotomy; (21E) marks the implant tails that are located periretinal; (21F) and (21G) mark the cross sectional depth location of the implant using optical coherence tomography; (21H) shows the RPE and nerve fiber layer; and (21I) is the choroid.
Figure 22:
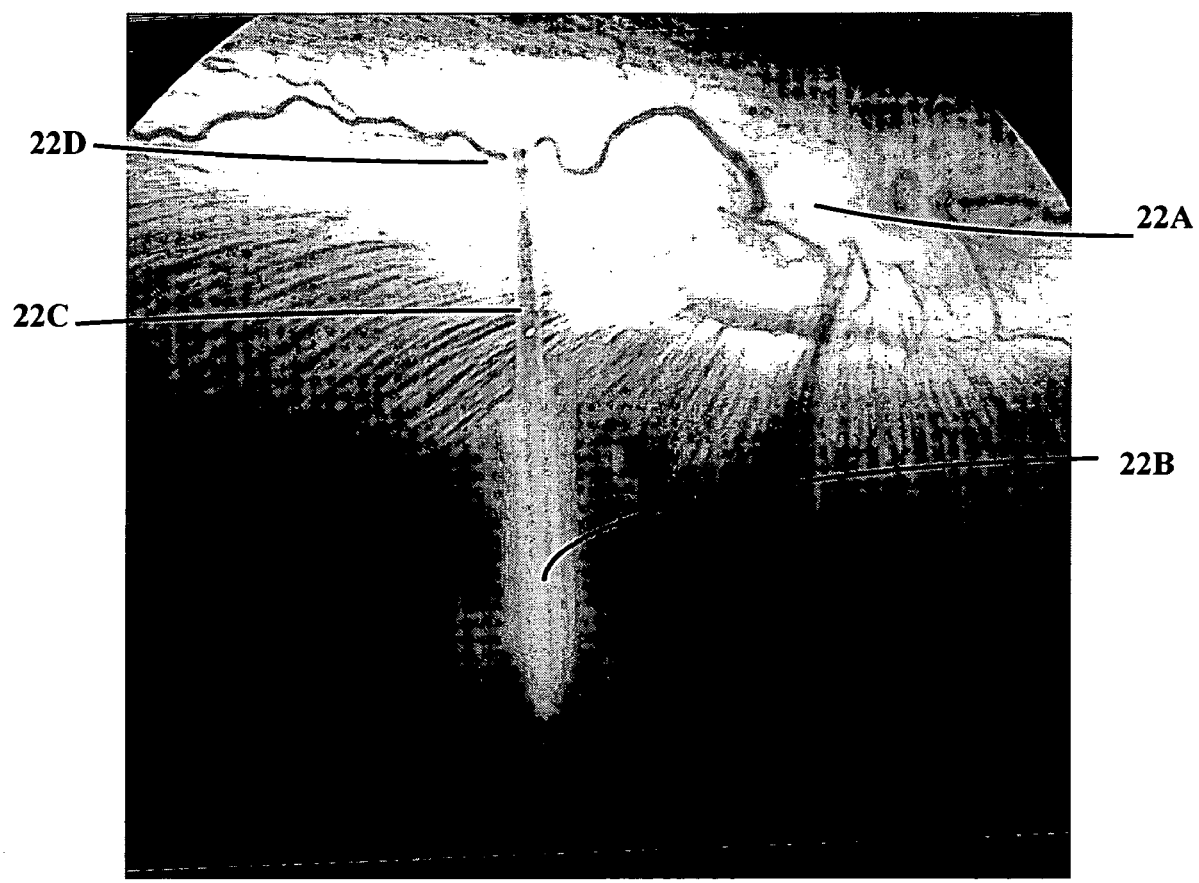
FIG. 22 shows a representative fundus photograph of a PMMA core subretinal implant loaded with rapamycin at one week implantation, where (22A) marks the optic nerve; (22B) marks the subretinal implant; (22C) shows the site of the retinotomy; and (22D) marks the implant tails that are located periretinal.

The single TiNi core subretinal implant shown in FIG. 20 can be contrasted with a double surgical implant shown in FIG. 21. In the surgical setting, the implantation of an array of drug delivery devices around the disease site could prove detrimental to controlling its proliferation. FIG. 22 shows a PMMA core implantation. Polymers such as PMMA have a long history in the ophthalmic industry with their use in contact and intraocular lenses, and may be better accepted than a metal implant. The chromic gut core implant also proved successful. Here, the concept was to implant the device, using the tail for grasping, and then to allow the tail segment to bioabsorb over time. Due to surgery scheduling, this rabbit was actually sacrificed after 45 days with no indication of inflammatory response and excellent biocompatibility of the bioabsorbable chromic gut suture material. The chromic gut core showed no signs of bioabsorption, even after 45 days. When used as a suture, the chromic gut is expected to be totally bioabsorbed within 90 days; but our results suggest it may have a lower biodegradation rate in this subretinal application.

The adverse surgical indications shown in Table 5, in particular in the exploratory group, were caused by instrument trauma to the lens and loss of flow rate control to the infusion line equipment that maintains the intraocular pressure. The results of the clinical indications are presented in Table 6. Other than the retinal indications, all adverse clinical findings (vitreous and anterior chamber) were seen in the rapamycin implant group. Rabbits 13 and 15 had vitreous inflammatory debris and iris synechia. Rabbit 14 had cells in the anterior chamber (that could ultimately lead to proliferation) and an abnormal pupillary shape. Rabbit 16 had corneal edema and a corneal ulceration. Rabbit 17 had corneal edema, a corneal ulceration and corneal neovascularization. Rabbit 18 had an abnormal pupillary shape, iris synechia and vitreous inflammatory debris. These clinical indications suggest rapamycin may be toxic to the rabbit eye at the current doses. The retinal indications were associated with microforceps trauma to the tissue and were not specific to a particular implant group.

Figure 23:
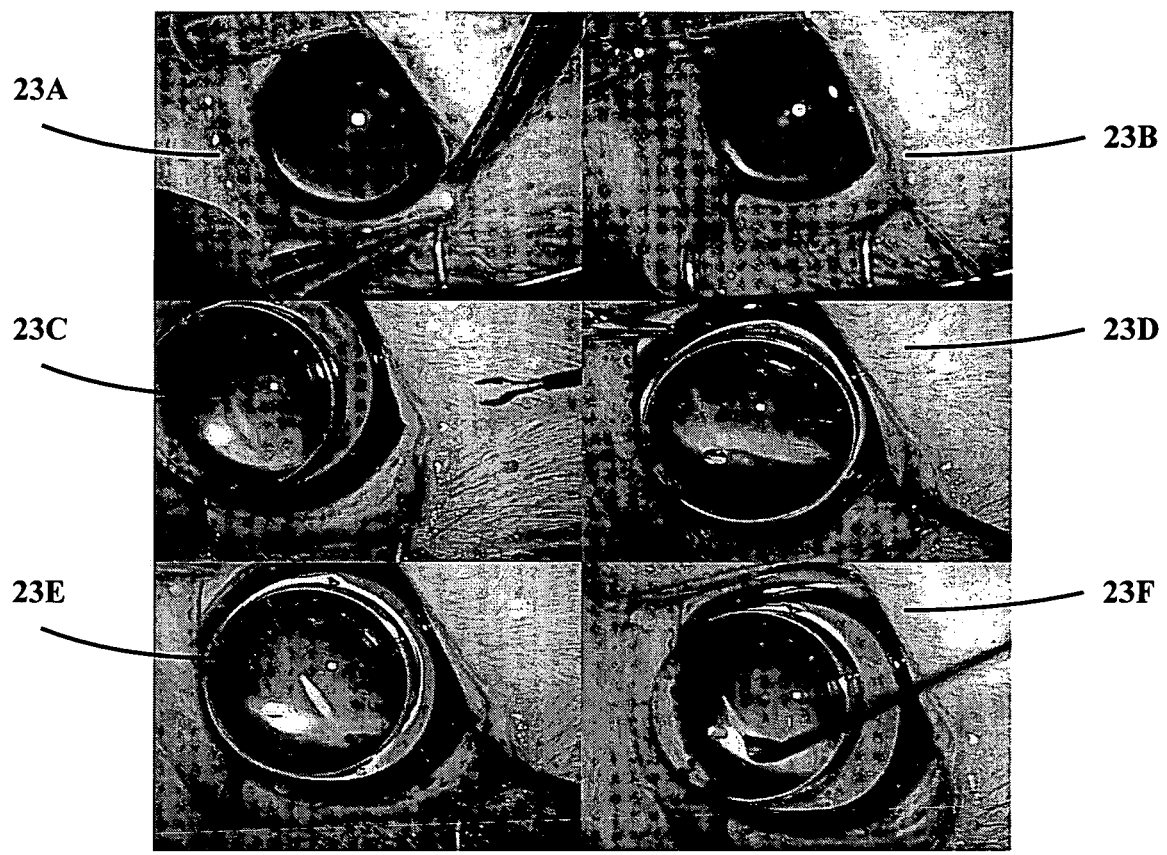
FIG. 23 shows a representative implant retrieval surgery where (23A) shows the conjunctival incision; (23B) shows the sclerotomy; (23C) shows the surgical microforceps; (23D) shows the microforceps extending through the vitreous to the retina to retrieve the implant; (23E) shows the microforceps grasping the tail of the implant; and (23F) shows the retrieved implant.

At the completion of the study, all implants were successfully retrieved. Removal of the implants from the subretinal space was faultless. Once the animal was anesthetized and prepared for surgery, the implant was retrieved in less than 5 minutes (FIG. 23). There was no adherent tissue that impeded the removal. Furthermore, the implants remained intact and did not appear encapsulated. The tails of the implants, which were left periretinal, facilitated the removal process. Changes in the surface microstructure and translucence of the drug-loaded implant were apparent and are associated with the formation of microporosities as the drug elutes. The implants with no drug did not change in appearance throughout the study, as was expected from these types of materials. Except for the rapamycin drug group, all rabbits were sacrificed with no indication of inflammatory response or changes in general health, which is an indication of good biocompatibility of the device.

The Example successfully demonstrated the use of a subretinal drug-delivery platform as an alternative to introducing drugs directly into the vitreous chamber of the eye by intraocular injection or intravitreal implant. The control group and triamcinolone implants showed good biocompatibility and efficacy while the rapamycin-loaded implants showed signs of toxicity at the current dose. Implant retrieval was an uncomplicated procedure. The implants were structurally intact, and for those that were drug-loaded, the surface began to develop porosities as the drug eluted.

TABLE 5

| | Animal Label | Implant 1 | Implant 2 | Total Dose | Comments |
|---|---|---|---|---|---|
| Group 1A Triamcinolone | 1 | TA2 | | 33.5 | |
| | 2 | TA3 | | 35.6 | |
| | 3 | TA10 | | 25.4 | |
| | 4 | TA5 | TA7 | 54.1 | |
| | 5 | TA6 | TA8 | 51.0 | |
| Group 2 Control | 6 | C3 | | 0 | Lost/ hemorrhage |
| | 7 | C4 | | 0 | |
| | 8 | C5 | C9 | 0 | |
| | 9 | C6 | | 0 | |
| | 10 | C7 | C10 | 0 | |
| Group 3A RAP Fast Release | 11 | RAF21 | RAF25 | 192.6 | |
| | 12 | RAF22 | | 105.0 | |
| | 13 | RAF23 | | 97.8 | |
| | 14 | RAF24 | | 97.2 | |
| | 15 | RAF26 | RAF28 | 195.6 | |
| Group 3B RAP Slow Release | 16 | RAS11 | | 100.2 | Lensectomy |
| | 17 | RAS5 | | 96.0 | Lensectomy |
| | 18 | RAS6 | RAS10 | 202.8 | |
| Group 4 RAP Fast Release | EX1 | PMMA1 | | 78.6 | |
| | EX2 | PMMA2 | | 72.6 | Lost/ detachment |
| | EX3 | PMMA3 | | 68.4 | Lensectomy |
| | EX4 | Chromic Gut 1 | | 58.8 | Lost/ detachment |
| | EX5 | Chromic Gut 2 | | 122.4 | Lost/ detachment |
| | EX6 | Chromic Gut 3 | | 96.0 | Lensectomy |

TABLE 6

| Region | Evaluation | 24 B | 24 S | 20 1 D* | 20 1 W | 20 2 W | 20 4 W |
|---|---|---|---|---|---|---|---|
| Conjunctiva | Redness | 0 | 0 | 20 | 4 | 0 | 0 |
| | Chemosis | 0 | 0 | 0 | 0 | 0 | 0 |
| | Extrusion of implant | 0 | 0 | 0 | 0 | 0 | 0 |
| | Thinning | 0 | 0 | 0 | 0 | 0 | 0 |
| | Lesions | 0 | 0 | 0 | 0 | 0 | 0 |
| | Fibrous growth | 0 | 0 | 0 | 0 | 0 | 0 |
| | Mucous discharge | 0 | 0 | 17 | 0 | 0 | 0 |
| Cornea | Neovascularization | 0 | 0 | 0 | 1 | 1 | 1 |
| | Ulceration | 0 | 0 | 0 | 2 | 0 | 0 |
| | Edema | 0 | 0 | 0 | 3 | 1 | 2 |
| Lens | Cataract | 0 | 0 | | 2 | 2 | 2 |
| | Lens halo | 0 | 0 | | 0 | 0 | 0 |
| Anterior chamber | Flare | 0 | 0 | | 0 | 0 | 0 |
| | Cells | 0 | 0 | | 0 | 0 | 1 |
| | Pupillary shape | 0 | 0 | | 2 | 2 | 6 |
| Iris | Vascular hyperemia | 0 | 0 | | 0 | 0 | 0 |
| | Rubeosis iridis | 0 | 0 | | 0 | 0 | 0 |
| | Swelling | 0 | 0 | | 0 | 0 | 0 |
| | Synechia | 0 | 0 | | 0 | 1 | 3 |
| Vitreous | Inflammatory debris/vitreous strand | 0 | 0 | | 0 | 2 | 3 |
| | Hemorrhage | 0 | 0 | | 0 | 0 | 0 |
| Retina | Trauma/Tear (Other than retinotomy) | 0 | 6 | | 3 | 2 | 2 |
| | Detachment | 0 | 3 | | 0 | 0 | 0 |
| | White patch/retinal lesions | 0 | 0 | | 0 | 0 | 0 |
| | Hemorrhage | 0 | 5 | | 7 | 7 | 3 |
| Insertion site | Peri device bleeding | | 0 | | 0 | 3 | 0 |
| | Extrusion of device | | 0 | | 0 | 0 | 0 |

B = Baseline
S = Surgery;
D = Day;
W = Week
*Visual examination only

Description of Supporting FIGS.

FIG. 20 shows a a representative fundus photograph and optical coherence tomography of a single TiNi core subretinal implant loaded with triamcinolone acetonide at four weeks implantation, where (20A) marks the optic nerve; (20B) marks the subretinal implant; (20C) shows the site of the retinotomy; (20D) marks the implant tails that are located periretinal; (20E) marks the cross sectional depth location of the implant using optical coherence tomography; (20F) shows the RPE and nerve fiber layer; (20G) is a local retinal detachment surrounding the implant; and (20H) is the choroid.

FIG. 21 shows a representative fundus photograph and optical coherence tomography of a double TiNi core subretinal implant loaded with triamcinolone acetonide at one week implantation, where (21A) marks the optic nerve; (21B) and (21C) mark the subretinal implants; (21D) shows the site of the retinotomy; (21E) marks the implant tails that are located periretinal; (21F) and (21G) mark the cross sectional depth location of the implant using optical coherence tomography; (21H) shows the RPE and nerve fiber layer; and (21I) is the choroid.

FIG. 22 shows a representative fundus photograph of a PMMA core subretinal implant loaded with rapamycin at one week implantation, where (22A) marks the optic nerve; (22B) marks the subretinal implant; (22C) shows the site of the retinotomy; and (22D) marks the implant tails that are located periretinal.

FIG. 23 shows a representative implant retrieval surgery where (23A) shows the conjunctival incision; (23B) shows the sclerotomy; (23C) shows the surgical microforceps; (23D) shows the microforceps extending through the vitreous to the retina to retrieve the implant; (23E) shows the microforceps grasping the tail of the implant; and (23F) shows the retrieved implant.

Other embodiments of this invention will be apparent to those skilled in the art upon consideration of this specification or from practice of the invention disclosed herein. Various omissions, modifications, and changes to the principles and embodiments described herein may be made by one skilled in the art without departing from the true scope and spirit of the invention which is indicated by the following claims. All patents, patent documents, and publications cited herein are hereby incorporated by reference as if individually incorporated.

What is claimed is:

1. A sustained release implant that is configured for placement in a subretinal area of an eye having a choroid, a retina, one or more tissue layers above the choroid, and a nerve fiber layer, the sustained release implant comprising:
   a central longitudinally-extending solid biocompatible core having a length and a continuous outer surface area; wherein the biocompatible core comprises a nondegradable and non-polymer material; and
   a biocompatible coating layer comprising a polymer matrix and a bioactive agent that is applied over at least a portion of the outer surface area of the core;
   wherein the implant is configured to be positioned in one or more tissue layers above the choroid but below the nerve fiber layer of the eye; wherein the core has a diameter of about 200 or less; and the implant has a total diameter of about 500 μm or less; and a length no greater than about 5 mm.

2. The implant of claim 1 wherein the coating layer is applied over the entire length of the biocompatible core.

3. The implant of claim 1 wherein the coating layer is applied over a portion of the length of the biocompatible core and wherein one or more portions of the length of the biocompatible core are left uncoated.

4. The implant of claim 1 wherein the coating layer comprises a center portion, a proximal transition segment, and a distal transition segment.

5. The implant of claim 4 wherein at least one of the proximal transition segment or the distal transition segment are feathered.

6. The implant of claim 5 wherein both the proximal transition segment and the distal transition segment are feathered.

7. The implant of claim 1 wherein the biocompatible core or biocompatible coating layer comprises a biostable polymer.

8. The implant of claim 7 wherein the biostable polymer is selected from the group consisting of polyurethanes, silicones, polyesters, polyolefins, polyisobutylene, acrylic polymers, vinyl halide polymers, polyvinyl ethers, polyvinyl methyl ether, polyvinylidene halides, polyacrylonitrile, polyvinyl ketones, polyvinyl aromatics, polyvinyl esters, poly(alkyl(meth)acrylates, such as poly((methyl)methacrylate) or poly((butyl)methacrylate)), polyvinyl amides, polyamides, polycaprolactam, polycarbonates, polyoxymethylenes, polyimides, polyethers, polyurethanes, rayon, rayon-triacetate, cellulose acetate, cellulose butyrate, cellophane, cellulose nitrate, cellulose propionate, cellulose ethers, carboxymethyl cellulose, copolymers thereof and blends thereof.

9. The implant of claim 1 wherein the biocompatible coating layer comprises a biodegradable polymer or a biodegradable material.

10. The implant of claim 9 wherein the biodegradable polymer is selected from the group consisting of poly(L-lactic acid), poly(caprolactone) poly(lactide-co-glycolide), poly(hydroxybutyrate), poly(hydroxybutyrate-co valerate), polydioxanone, polyorthoesters, polyanhydrides, poly(glycolic acid), poly(D,L lactic acid), poly(glycolic acid-co-trimethylene carbonate), poly(phosphate esters), polyphosphoester urethanes, poly(amino acids), cyanoacrylates, poly (trimethylene carbonates), polycarbonates, poly (iminocarbonates), polyesters, copoly(ether-esters), polyalkylene oxalates, polyphosphazenes and copolymers and blends of the above polymers.

11. The implant of claim 9 wherein the biodegradable material is selected from the group consisting of fibrin, fibrinogen, cellulose, dextrans, polysaccharides, starch collagen, chromic gut, and hyaluronic acid.

12. The implant of claim 1 wherein the biocompatible core comprises a material selected from the group consisting of titanium-nickel alloy wire, titanium alloy, nickel-cobalt base alloys, stainless steel, cobalt-chromium alloy, and biodegradable magnesium alloys.

13. The implant of claim 1 wherein the implant has a total diameter that ranges from about 200 μm to about 500 μm.

14. The implant of claim 1 wherein the implant has a total length that ranges from about 2.25 mm to about 2.75 mm.

15. The implant of claim 1 wherein the core has a cross-sectional shape that is circular.

16. The implant of claim 1 wherein the biocompatible coating layer is covered with one or more additional coating layers of polymer material whereby the one or more additional coating layers of polymer material modify the release rate characteristics of the bioactive agents from the polymer matrix.

17. The implant of claim 16 wherein the one or more additional coating layers comprise poly(caprolactone), poly (methylmethacrylate), polyesters, chromic gut, polyorthoesters, polypropylene, polyethylene vinyl acetate or poly(butylmethacrylate).

18. The implant of claim 1 wherein the bioactive agent is selected from antiproliferative agent, anti-inflammatory agent, anti-angiogenic agent, antibiotic, neurotrophic factor, or a combination thereof.

19. The implant of claim 1 wherein the polymer matrix comprises a blend of (a) a first biodegradable polymer that is a copolymer of polyalkylene glycol terephthalate and an aromatic polyester; and (b) a second biodegradable polymer; wherein the second biodegradable polymer is selected to have a slower bioactive agent release rate relative to the first biodegradable polymer.

20. The implant of claim 19 wherein the polyalkylene glycol terephthalate is selected from the group of polyethylene glycol terephthalate, polypropylene glycol terephthalate, polybutylene glycol terephthalate, and combinations of these.

21. The implant of claim 19 wherein the aromatic polyester comprises polyethylene terephthalate, polypropylene terephthalate, polybutylene terephthalate, and combinations thereof.

22. The implant of claim 19 wherein the first polymer comprises a copolymer of polyethylene glycol terephthalate and polybutylene terephthalate in relative amounts of 70-80% polyethylene glycol terephthalate and 5-20% polybutylene terephthalate.

23. The implant of claim 19 wherein the second biodegradable polymer comprises a polymer derived from monomers selected from lactic acid, glycolic acid, caprolactone, ethylene glycol, and ethyloxyphosphate.

24. The implant of claim 1 wherein the polymer matrix comprises a random block copolymer having the formula:

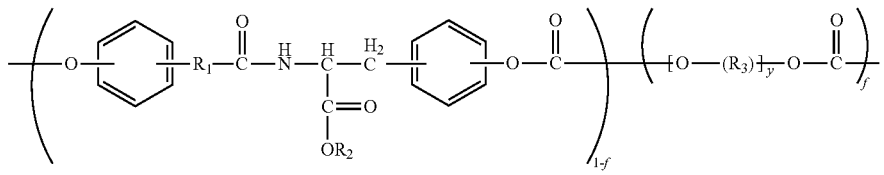

wherein R1 is —CH=CH— or (—CH$_2$—)$_j$, in which j is zero or an integer from one to eight;

R2 is selected from straight and branched alkyl and alkylaryl groups containing up to 18 carbon atoms and optionally containing at least one ether linkage, and derivatives of biologically or pharmaceutically active compounds covalently bonded to the copolymer;

each R3 is independently selected from alkylene groups containing 1 to 4 carbon atoms;

y is between 5 and about 3000; and f is the percent molar fraction of alkylene oxide in the copolymer.

25. The implant of claim 1 wherein the polymer matrix comprises a hydrogel.

26. The implant of claim 1, wherein the core has diameter of about 80 μm or less.

27. A sustained release implant that is configured for placement in a subretinal area of an eye having a choroid, a retina, one or more tissue layers above the choroid, and a nerve fiber layer, the sustained release implant comprising:

a central longitudinally-extending solid biocompatible core that has a length and a continuous outer surface; wherein the biocompatible core comprises a nondegradable and non-polymer material; and a biocompatible coating layer comprising a polymer matrix and a bioactive agent that is applied over at least a portion of the outer surface of the core;

wherein the core has a diameter of about 200 μm or less;

wherein the implant has a total diameter of about 500 μm or less and has a length no greater than about 5 mm;

wherein the biocompatible coating layer comprises a center portion, a proximal transition segment, and a distal transition segment; wherein at least one of the proximal transition segment or the distal transition segment are feathered.

28. A sustained release implant that is configured for placement in a subretinal area of an eye having a choroid, a retina, one or more tissue layers above the choroid, and a nerve fiber layer, the sustained release implant comprising:
- a central longitudinally-extending solid biocompatible core that has a length and a continuous outer surface; wherein the biocompatible core comprises a nondegradable and non-polymer material; and
- a biocompatible coating layer comprising a polymer matrix and a bioactive agent that is applied over at least a portion of the outer surface of the core;

wherein the core has a diameter of about 200 μm or less;
wherein the implant has a total diameter of about 500 μm or less and has a length no greater than about 5 mm;
wherein the biocompatible coating layer is applied over a portion of the length of the biocompatible core; and
wherein one or more portions of the length of the biocompatible core are left uncoated.

* * * * *

UNITED STATES PATENT AND TRADEMARK OFFICE
CERTIFICATE OF CORRECTION

| | | |
|---|---|---|
| PATENT NO. | : 8,003,124 B2 | Page 1 of 1 |
| APPLICATION NO. | : 11/399945 | |
| DATED | : August 23, 2011 | |
| INVENTOR(S) | : Signe E. Varner et al. | |

It is certified that error appears in the above-identified patent and that said Letters Patent is hereby corrected as shown below:

Column 46,
Line 37, "200 or less" should be --200 µm or less--

Signed and Sealed this
Eighteenth Day of October, 2011

David J. Kappos
*Director of the United States Patent and Trademark Office*